US006291665B1

(12) United States Patent
Gaffney et al.

(10) Patent No.: US 6,291,665 B1
(45) Date of Patent: Sep. 18, 2001

(54) FUNGAL TARGET GENES AND METHODS

(75) Inventors: Thomas Deane Gaffney, Chapel Hill; Albert Flavier, Raleigh; Krista Gates, Apex, all of NC (US); Jürgen Wendland, Jena (DE); Yasmina Ayad-Durieux; Fred Dietrich, both of Basel (CH); Peter Philippsen, Riehen (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 09/588,256

(22) Filed: Jun. 6, 2000

Related U.S. Application Data

(63) Continuation of application No. 08/335,937, filed on Nov. 8, 1994, now abandoned.

(51) Int. Cl.[7] .............................. C07H 21/04; C12N 1/21; C12N 1/15; C12N 15/00
(52) U.S. Cl. .................... 536/23.74; 435/252.3; 435/254.11; 435/320.1
(58) Field of Search ............................. 435/320.1, 252.3, 435/254.11; 536/23.1, 23.74

(56) References Cited

PUBLICATIONS

Samejima et al. Identification of cut8+ and cek1+, a novel protein kinase gene, which complement a fission yeast mutation that blocks anaphase. Mol. Cell. Biol. 1994, vol. 14, pp. 6361–6371.*
Nasr et al. The sequence of 36.8 kb from the left arm of chromosome XIV reveals 24 complete open reading frames: 18 correspond to new genes, one of which encodes a protein similar to the human myotonic dystrophy kinase. Yeast. 1996, vol. 12, pp. 169–175.*
Lauter et al. Photoregulation of cot–1, a kinase–encoding gene involved in hyphal growth in Neurospora crassa. Fungal Genetics and Biology. Apr. 1998, vol. 23, pp. 300–310.*
Durrenberger et al. The ukc1 gene encodes a protein kinase involved in morphogenesis, pathogenicity and pigment formation in Ustilago maydis. Mol. Gen. Genet. Mar. 1999, vol. 261, pp. 281–289.*
Verde et al. Fission yeast orb6, a ser/thr protein kinase related to mammalian rho kinase and myotonic dystrophy kinase,is required for maintenance of cell polarity and coordinates cell morphogenesis with the cell cycle. PNAS USA. Jun. 23, 1998, vol. 95,p.7526.*
Benton, B.K. et al., Molecular and Cellular Biology, 17(9): pp. 5067–5076 (1997).
Buhr, T.L. et al., Mol Gen Genet, 251: pp.565–572 (1996).
Chen, G.–C. et al., Genes & Development, 11: pp.2958–2971 (1997).
Davis, C.R. et al., Journal of Biological Chemistry, 273(2): pp.849–858 (1998).
Eby, J.J. et al., Current Biology, 8(17): pp.967–970 (1998).
Emili, A. et al., Proc. Natl. Acad. Sci. USA, 95: pp.11122–11127 (1998).
Leberer, E. et al., Current Biology, 7(8): pp.539–546 (1997).
Manser, E. et al., Molecular and Cellular Biology, 17(3): pp.1129–1143 (1997).
Oehlen, L.J.W.M. and Cross, F.R., Journal of Biology Chemistry, 273(39): pp.25089–25097 (1998).
Tjandra, H. et al., Current Biology, 8(18): pp.991–1000 (1998).
Wu, C. et al., Journal of Biological Chemistry, 271(50): pp.31787–31790 (1996).
Wu, C. et al., Journal of Biological Chemistry, 272(49): pp.30623–30626 (1997).
Yarden, O. et al., EMBO Journal, 11(6): pp.2159–2166 (1992).

* cited by examiner

*Primary Examiner*—James Ketter
*Assistant Examiner*—Lisa J. Gansheroff
(74) *Attorney, Agent, or Firm*—Bruce Vrana

(57) ABSTRACT

The invention relates to genes isolated from *Ashbya gossypii* that code for proteins essential for normal fungal growth and development. The invention also includes the methods of using these proteins to discover new fungicides, based on the essentiality of the gene for normal growth and development. The invention can also be used in a screening assay to identify inhibitors that are potential fungicides.

16 Claims, No Drawings

FUNGAL TARGET GENES AND METHODS

This application is a continuation of application Ser. No. 08/335,937, filed Nov. 8, 1994, now abandoned. The disclosure of this priority document is hereby expressly incorporated by reference in its entirety into the instant disclosure.

FIELD OF THE INVENTION

The invention relates to genes isolated from *Ashbya gossypii* that encode proteins essential for fungal growth and development. The invention also includes the methods of using these proteins as fungal targets, based on the essentiality of these genes for normal fungal growth and development. The invention is also useful as a screening assay to identify inhibitors that are potential fungicides.

BACKGROUND OF THE INVENTION

The phytopathogenic fungus *Ashbya gossypii* is a filamentously growing ascomycete that was first isolated as a plant pathogen in tropical and sub-tropical regions. It infects the seed capsule of cotton plants (Ashby S. F. and Nowell W. (1926) Ann. Botany 40: 69–84) and has also been isolated from tomatoes and citrus fruits (Phaff H. J. and Starmer W. T. (1987) In "The Yeasts", Vol. I Rose A. H., Harrison, J. S. (eds), Academic Press, London, 123 ff; Dammer K. H. and Ravelo H. G. (1990). Arch. Phytopathol. Pflanzenschutz, Berlin 26: 71–78 Dammer and Ravelo, 1990). The infection of the seed capsule is caused by transmission of *A. gossypii* mycelium pieces or spores by stinging-sucking insects and causes a disease called stigmatomycosis.

Studies characterising the karyotype of *A. gossypii* have been performed (Wright, 1990; Wendland, 1993; Gaudenz, 1994, "The small genome of the filamentous fungus *Ashbya gossypii*: Assessment of the karyotype", Diploma Thesis, Department of Applied Microbiology, Biocenter, University Basel). It has been found using yeast chromosomes of precisely known length as size markers that the genome of *A. gossypii* has a total nuclear genome size of 8.85 Mb. Presently, *A. gossypii* represents the most compact eukaryotic genome, compared to genome sizes of 12.5 Mb for *Saccharomyces cerevisiae* (Chu et al. (1986) Science, 234:1582–1585), 31.0 Mb for *Aspergillus nidulans* (Brody and Carbon (1989) Proc Natl Acad Sci USA. 86:6260–6263), and 47.0 Mb for *Neurospora crassa* (Orbach et al.(1988) Mol Cell Biology, 8:1469–1473).

*A. gossypii* is systematically grouped to the endomycetales belonging to the family of spermophthoraceae. This classification is based on the observation that the spores that develop in hyphal compartments called sporangia look like ascospores, which are defined as end products of meiosis.

Since *A. gossypii* is a filamentous ascomycete, and is capable of growing only by filamentous (hyphal) growth, fungal targets found in this model organism are predictive of targets which will be found in other pathogens, the vast majority of which grow in a filamentous fashion.

SUMMARY OF THE INVENTION

It is an object of the invention to provide an effective and beneficial method to identify novel fungicides. A feature of the invention is the identification of genes in *A. gossypii* having a putative biological activity based on their similarity to yeast genes. Genes of the invention comprise a putative serine/threonine protein kinase gene (herein referred to as AG007 gene), three genes of unknown function (AG008, AG009, AG010), and a putative serine/threonine protein kinase (AG011). Another feature of the invention is the discovery that the genes of the invention, AG007 (SEQ ID NO:1), AG008 (SEQ ID NO:3), AG009 (SEQ ID NO:5), AG010 (SEQ ID NO:7), and AG011 (SEQ ID NO:9) are essential for fungal growth and development. An advantage of the present invention is that the newly discovered essential genes provide the basis for identity of a novel fungicidal mode of action which enables one skilled in the art to easily and rapidly discover novel inhibitors of gene function useful as fungicides.

One object of the present invention is to provide an essential gene in fungi for assay development for inhibitory compounds with fungicidal activity. Genetic results show that when any of the genes described above are mutated in *A. gossypii*, the resulting phenotype ranges from suppressed growth to lethality. Suppressed growth as used herein results in a growth rate of half the growth rate observed in wild-type, or lower, e.g. 10% to 50% of the wild-type growth rate is observed, or no growth is detected at all macroscopically. Furthermore, when some of the genes described above are mutated in *A. gossypii*, abnormal filament development is observed. This demonstrates a critical role for the gene products encoded by these genes.

Using PCR-based gene disruption, the inventors of the present invention have demonstrated that the activities of these gene products are essential for *A. gossypii* growth. Thus, chemicals which inhibit the function of any of these gene products in fungi are likely to have detrimental effects on fungi, and are potentially good fungicide candidates. The present invention therefore provides methods of using a purified protein encoded by either the AG007, AG008, AG009, AG010, or AG011 gene, described below to identify inhibitors thereof, which can then be used as fungicides to suppress the growth of pathogenic fungi. Pathogenic fungi are defined as those capable of colonizing a host and causing disease. Examples of fungal pathogens include plant pathogens such as *Septoria tritici*, *Stagnospora nodorum*, *Botrytis cinerea*, *Fusarium graminearum*, *Magnaporthe grisea*, *Cochliobolus heterostrophus*, *Colletotrichum heterostrophus*, *Ustilago maydis*, *Erisyphe graminis*, plant pathogenic oomycetes such as *Pythium ultimum* and *Phytophthora infestans*, and human pathogens such as *Candida albicans* and *Aspergillus fumigatus*.

The present invention discloses novel nucleotide sequences derived from *A. gossypii*, designated the AG007, AG008, AG009, AG010, and AG011 genes. The nucleotide sequence of the ORF in the genomic clones is set forth in SEQ ID NO:1 (AG007), SEQ ID NO:3 (AG008), SEQ ID NO:5 (AG009), SEQ ID NO:7 (AG010), and SEQ ID NO:9 (AG011). The amino acid sequences encoded by the above sequences are set forth in SEQ ID NO:2 (AG007), SEQ ID NO:4 (AG008), SEQ ID NO:6 (AG009), SEQ ID NO:8 (AG010), and SEQ ID NO:10 (AG011), respectively. The present invention also includes nucleotide sequences substantially similar to those set forth in SEQ ID NO:1, SEQ ID NO:3, SEQ ID NO:5, SEQ ID NO:7, and SEQ ID NO:9. The present invention also encompasses fungal proteins whose amino acid sequences are substantially similar to the amino acid sequences set forth in SEQ ID NO:2, SEQ ID NO:4, SEQ ID NO:6, SEQ ID NO:8, and SEQ ID NO:10. The present invention also includes methods of using these gene products as fungal targets, based on the essentiality of the genes for normal fungal growth and development. Furthermore, the invention can be used in a screening assay to identify inhibitors of AG007, AG008, AG009, AG010, or AG011 gene function that are potential fungicides.

Other objects and advantages of the present invention will become apparent to those skilled in the art from a study of the following description of the invention and non-limiting examples.

DEFINITIONS

For clarity, certain terms used in the specification are defined and presented as follows:

Cofactor: natural reactant, such as an organic molecule or a metal ion, required in an enzyme-catalyzed reaction. A co-factor is e.g. NAD(P), riboflavin (including FAD and FMN), folate, molybdopterin, thiamin, biotin, lipoic acid, pantothenic acid and coenzyme A, S-adenosylmethionine, pyridoxal phosphate, ubiquinone, menaquinone. Optionally, a co-factor can be regenerated and reused.

DNA shuffling: DNA shuffling is a method to rapidly, easily and efficiently introduce mutations or rearrangements, preferably randomly, in a DNA molecule or to generate exchanges of DNA sequences between two or more DNA molecules, preferably randomly. The DNA molecule resulting from DNA shuffling is a shuffled DNA molecule that is a non-naturally occurring DNA molecule derived from at least one template DNA molecule. The shuffled DNA encodes an enzyme modified with respect to the enzyme encoded by the template DNA, and preferably has an altered biological activity with respect to the enzyme encoded by the template DNA.

Enzyme activity: means herein the ability of an enzyme to catalyze the conversion of a substrate into a product. A substrate for the enzyme comprises the natural substrate of the enzyme but also comprises analogues of the natural substrate which can also be converted by the enzyme into a product or into an analogue of a product. The activity of the enzyme is measured for example by determining the amount of product in the reaction after a certain period of time, or by determining the amount of substrate remaining in the reaction mixture after a certain period of time. The activity of the enzyme is also measured by determining the amount of an unused co-factor of the reaction remaining in the reaction mixture after a certain period of time or by determining the amount of used co-factor in the reaction mixture after a certain period of time. The activity of the enzyme is also measured by determining the amount of a donor of free energy or energy-rich molecule (e.g. ATP, phosphoenolpyruvate, acetyl phosphate or phosphocreatine) remaining in the reaction mixture after a certain period of time or by determining the amount of a used donor of free energy or energy-rich molecule (e.g. ADP, pyruvate, acetate or creatine) in the reaction mixture after a certain period of time.

Fungicide: a chemical substance used to kill or suppress the growth of fungal cells.

Heterologous DNA Sequence: a DNA sequence not naturally associated with a host cell into which it is introduced, including non-naturally occurring multiple copies of a naturally occurring DNA sequence; and genetic constructs wherein an otherwise homologous DNA sequence is operatively linked to a non-native sequence.

Homologous DNA Sequence: a DNA sequence naturally associated with a host cell into which it is introduced.

Inhibitor: a chemical substance that causes abnormal growth, e.g., by inactivating the enzymatic activity of a protein such as a biosynthetic enzyme, receptor, signal transduction protein, structural gene product, or transport protein that is essential to the growth or survival of the fungus. In the context of the instant invention, an inhibitor is a chemical substance that alters the enzymatic activity encoded by the AG007, AG008, AG009, AG010, or AG011 genes from a fungus. More generally, an inhibitor causes abnormal growth of a host cell by interacting with the gene product encoded by the AG007, AG008, AG009, AG010, or AG011 genes.

Isogenic: fungi which are genetically identical, except that they may differ by the presence or absence of a heterologous DNA sequence.

Isolated: in the context of the present invention, an isolated DNA molecule or an isolated enzyme is a DNA molecule or enzyme that, by the hand of man, exists apart from its native environment and is therefore not a product of nature. An isolated DNA molecule or enzyme may exist in a purified form or may exist in a non-native environment such as, for example, in a transgenic host cell.

Minimal Promoter: promoter elements, particularly a TATA element, that are inactive or that have greatly reduced promoter activity in the absence of upstream activation. In the presence of a suitable transcription factor, the minimal promoter functions to permit transcription.

Modified Enzyme Activity: enzyme activity different from that which naturally occurs in a fungus (i.e. enzyme activity that occurs naturally in the absence of direct or indirect manipulation of such activity by man), which is tolerant to inhibitors that inhibit the naturally occurring enzyme activity.

Significant Increase: an increase in enzymatic activity that is larger than the margin of error inherent in the measurement technique, preferably an increase by about 2-fold or greater of the activity of the wild-type enzyme in the presence of the inhibitor, more preferably an increase by about 5-fold or greater, and most preferably an increase by about 10-fold or greater.

Significantly less: means that the amount of a product of an enzymatic reaction is reduced by more than the margin of error inherent in the measurement technique, preferably a decrease by about 2-fold or greater of the activity of the wild-type enzyme in the absence of the inhibitor, more preferably an decrease by about 5-fold or greater, and most preferably an decrease by about 10-fold or greater.

In its broadest sense, the term "substantially similar", when used herein with respect to a nucleotide sequence, means a nucleotide sequence corresponding to a reference nucleotide sequence, wherein the corresponding sequence encodes a polypeptide having substantially the same structure and function as the polypeptide encoded by the reference nucleotide sequence, e.g. where only changes in amino acids not affecting the polypeptide function occur. Desirably the substantially similar nucleotide sequence encodes the polypeptide encoded by the reference nucleotide sequence. The term "substantially similar" is specifically intended to include nucleotide sequences wherein the sequence has been modified to optimize expression in particular cells. The percentage of identity between the substantially similar nucleotide sequence and the reference nucleotide sequence desirably is at least 65%, more desirably at least 75%, preferably at least 85%, more preferably at least 90%, still more preferably at least 95%, yet still more preferably at least 99%. Sequence comparisons are carried out using a Smith-Waterman sequence alignment algorithm (see e.g. Waterman, M. S. Introduction to Computational Biology: Maps, sequences and genomes. Chapman & Hall. London: 1995. ISBN 0-412-99391-0. The localS program, version 1.16, is used with following parameters: match: 1, mismatch penalty: 0.33, open-gap penalty: 2, extended-gap penalty: 2. A nucleotide sequence "substantially similar" to reference nucleotide sequence hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NAPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1 ×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C. As used herein the term "AG007, AG008, AG009, AG010, or AG011 gene" refers to a DNA molecule comprising SEQ ID NO:1, SEQ ID NO:3, SEQ ID NO:5, SEQ ID NO:7, or SEQ ID NO:9 or comprising a nucleotide sequence substantially similar to SEQ ID NO: 1, SEQ ID NO:3, SEQ ID NO:5, SEQ ID NO:7, or SEQ ID NO:9. Homologs of these genes include nucleotide sequences that encode an amino acid sequence that is at least 25% identical to SEQ ID NO:2, SEQ ID NO:4, SEQ ID NO:6, SEQ ID NO:8, or SEQ ID NO:10 as measured, using the parameters described below, wherein the amino acid sequence encoded by the homolog has the biological activity of the AG007, AG008, AG009, AG010, or AG011 protein.

The term "substantially similar", when used herein with respect to a protein, means a protein corresponding to a reference protein, wherein the protein has substantially the same structure and function as the reference protein, e.g. where only changes in amino acids sequence not affecting the polypeptide function occur. When used for a protein or an amino acid sequence the percentage of identity between the substantially similar and the reference protein or amino acid sequence desirably is at least 65%, more desirably at least 75%, preferably at least 85%, more preferably at least 90%, still more preferably at least 95%, yet still more preferably at least 99%, using default BLAST analysis parameters BLAST 2.0.7. As used herein the term "AG007, AG008, AG009, AG010, or AG011 protein" refers to an amino acid sequence encoded by a DNA molecule comprising a nucleotide sequence substantially similar to SEQ ID NO:1, SEQ ID NO:3, SEQ ID NO:5, SEQ ID NO:7, or SEQ ID NO:9. Homologs of the AG007, AG008, AG009, AG010, or AG011 proteins are amino acid sequences that are at least 25% identical to SEQ ID NO:2, SEQ ID NO:4, SEQ ID NO:6, SEQ ID NO:8, or SEQ ID NO:10 as measured using the parameters described above, wherein the amino acid sequence encoded by the homolog has the biological activity of the AG007, AG008, AG009, AG010, or AG011 protein.

Substrate: a substrate is the molecule that an enzyme naturally recognizes and converts to a product in the biochemical pathway in which the enzyme naturally carries out its function, or is a modified version of the molecule, which is also recognized by the enzyme and is converted by the enzyme to a product in an enzymatic reaction similar to the naturally-occurring reaction.

Tolerance: the ability to continue essentially normal growth or function when exposed to an inhibitor or fungicide in an amount sufficient to suppress the normal growth or function of native, unmodified fungi.

Transformation: a process for introducing heterologous DNA into a cell, tissue, or fungus. Transformed cells, tissues, or fungi are understood to encompass not only the end product of a transformation process, but also transgenic progeny thereof.

Transgenic: stably transformed with a recombinant DNA molecule that preferably comprises a suitable promoter operatively linked to a DNA sequence of interest.

BRIEF DESCRIPTION OF THE SEQUENCES IN THE SEQUENCE LISTING

SEQ ID NO:1 Genomic DNA coding sequence for the *Ashbya gossypii* AG007 gene
SEQ ID NO:2 Amino acid sequence encoded by the *Ashbya gossypii* AG007 DNA sequence shown in SEQ ID NO:1
SEQ ID NO:3 Genomic DNA coding sequence for the *Ashbya gossypii* AG008 gene
SEQ ID NO:4 Amino acid sequence encoded by the *Ashbya gossypii* AG008 DNA sequence shown in SEQ ID NO:3
SEQ ID NO:5 Genomic DNA coding sequence for the *Ashbya gossypii* AG009 gene
SEQ ID NO:6 Amino acid sequence encoded by the *Ashbya gossypii* AG009 DNA sequence shown in SEQ ID NO:5
SEQ ID NO:7 Genomic DNA coding sequence for the *Ashbya gossypii* AG010 gene
SEQ ID NO:8 Amino acid sequence encoded by the *Ashbya gossypii* AG010 DNA sequence shown in SEQ ID NO:7
SEQ ID NO:9 Genomic DNA coding sequence for the *Ashbya gossypii* AG011 gene
SEQ ID NO:10 Amino acid sequence encoded by the *Ashbya gossypii* AG011 DNA sequence shown in SEQ ID NO:9
SEQ ID NO:11 oligonucleotide primer S1
SEQ ID NO:12 oligonucleotide primer S2
SEQ ID NO:13 oligonucleotide primer G2
SEQ ID NO:14 oligonucleotide primer G3
SEQ ID NO:15 oligonucleotide primer AG007, S1
SEQ ID NO:16 oligonucleotide primer AG007, S2
SEQ ID NO:17 oligonucleotide primer AG008, S1
SEQ ID NO:18 oligonucleotide primer AG008, S2
SEQ ID NO:19 oligonucleotide primer AG009, S1
SEQ ID NO:20 oligonucleotide primer AG009, S2
SEQ ID NO:21 oligonucleotide primer AG010, S1
SEQ ID NO:22 oligonucleotide primer AG010, S2
SEQ ID NO:23 oligonucleotide primer AG011, S1
SEQ ID NO:24 oligonucleotide primer AG010, S2

DETAILED DESCRIPTION OF THE INVENTION

In a preferred embodiment, the proteins having AG007, AG008, AG009, AG010, and AG011 activities are encoded by nucleotide sequences derived from fungi, preferably filamentous fungi, particularly from *Ashbya gossypii*, desirably identical or substantially similar to the nucleotide sequences set forth in SEQ ID NO:1, SEQ ID NO:3, SEQ ID NO:5, SEQ ID NO:7, or SEQ ID NO:9. In another embodiment, the proteins having AG007, AG008, AG009, AG010, and AG011 activities are encoded by nucleotide sequences capable of encoding the amino acid sequences of SEQ ID NO:2, SEQ ID NO:4, SEQ ID NO:6, SEQ ID NO:8, or SEQ ID NO:10. In yet another embodiment, the proteins having AG007, AG008, AG009, AG010, and AG011 activities have amino acid sequences identical or substantially similar to the amino acid sequences set forth in SEQ ID NO:2, SEQ ID NO:4, SEQ ID NO:6, SEQ ID NO:8, or SEQ ID NO:10, respectively.

In a preferred embodiment, the present invention describes a method for identifying chemicals having the ability to inhibit any one or more of AG007, AG008, AG009, AG010, or AG011 activity in fungi preferably comprising the steps of: a) obtaining transgenic fungus and/or fungal cell, preferably stably transformed, comprising a non-native nucleotide sequence or an endogenous nucleotide sequences operably linked to non-native promoter, preferably an inducible promoter, encoding an enzyme having an activity and capable of overexpressing an enzymatically active AG007, AG008, AG009, AG010, or AG011 gene product where overexpression of the gene product suppresses or inhibits the normal growth and development of the fungus; b) applying a compound to the transgenic fungus and/or fungal cell c) determining the growth and/or development of the transgenic fungus and/or fungal cell after application of the compound; d) comparing the growth and/or development of the transgenic fungus and/or fungal cell after application of the chemical to the growth and/or development of the corresponding transgenic fungus and/or fungal cell to which the compound was not applied; and e) selecting compound that results in the growth and/or development of the transgenic fungus and/or fungal cell in comparison to the untreated transgenic fungus and/or fungal cell.

The invention also provides a method for suppressing the growth of a fungus comprising the step of applying to the fungus a compound that inhibits the naturally occurring AG007, AG008, AG009, AG010, and/or AG011 activity in the fungus. Normal growth is defined as a growth rate substantially similar to that observed in wild type fungus, preferably greater than at least 50% the growth rate observed in wild type fungus and particularly greater than 10% the growth rate observed in wild type fungus. Normal growth and development may also be defined, when used in relation to filamentous fungi, as normal filament development (including normal septation, normal nuclear migration and distribution), normal sporulation, and normal production of any infection structures (e.g. appressoria). Conversely, suppressed or inhibited growth as used herein is defined as less than half the growth rate observed in wild type or lower where 10% that of the wild-type growth rate is observed or no growth is macroscopically detected at all or abnormal filament development.

In a further embodiment according to the invention, a DNA sequence selected from the Sequence Listing may also be used for distinguishing among different species of plant pathogenic fungi and for distinguishing fungal pathogens from other pathogens such as bacteria.

I. Essentiality of the AG007, AG008, AG009, AG010, and AG011 Genes in *Ashbya gossypii* Demonstrated by Gene Disruption As shown in the examples below, the identification of a novel gene structure, as well as the essentiality of the AG007, AG008, AG009, AG010, and AG011 genes for normal fungal growth and development, have been demonstrated for the first time in *A. gossypii* using gene disruption. Having established the essentiality of AG007, AG008, AG009, AG010, and AG011 function in fungi and having identified the genes encoding these essential activities, the inventors thereby provide an important and sought after tool for new fungicide development.

II. Sequence of the *Ashbya gossypii* Genes

The present invention discloses the genomic nucleotide sequence of the *A. gossypii* AG007, AG008, AG009, AG010, and AG011 genes as well as the amino acid sequences of the *A. gossypii* AG007, AG008, AG009, AG010, and AG011 proteins. The nucleotide sequence corresponding to the genomic DNA coding region is set forth in SEQ ID NO:1, SEQ ID NO:3, SEQ ID NO:5, SEQ ID NO:7, and SEQ ID NO:9, and the amino acid sequence encoding the protein is set forth in SEQ ID NO:2, SEQ ID NO:4, SEQ ID NO:6, SEQ ID NO:8, and SEQ ID NO:10, respectively. The present invention also encompasses an isolated amino acid sequence derived from a fungus, wherein said amino acid sequence is identical or substantially similar to the amino acid sequence encoded by the nucleotide sequence set forth in SEQ ID NO:1, SEQ ID NO:3, SEQ ID NO:5, SEQ ID NO:7, or SEQ ID NO:9, wherein said amino acid sequence has AG007, AG008, AG009, AG010, or AG011 activity, respectively. Using BLASTX (2.0.7) programs with the default settings, notable sequence similarities are summarized below.

| Reference Amino Acid Sequence | Genbank Accession # | % Amino Acid Identity |
| --- | --- | --- |
| AG007 | Z71437[1] | 71 |
| AG008 | U00062[2] | 40 |
| AG009 | U28374[3] | 62 |
| AG010 | Q07953[4] | 70 |
| AG011 | Z71574[5] | 62 |
| AG011 | Z74855[6] | 60–65 |

[1]*Saccharomyces cerevisiae* gene YNL161w
[2]*S. cerevisiae* gene YHR040w
[3]*S. cerevisiae* gene YDR296w
[4]*S. cerevisiae* gene YLR022c
[5]*S. cerevisiae* gene YNL298w
[6]*S. cerevisiae* gene YOL113w III. Recombinant Production of AG007, AG008, AG009, AG010, or AG011 Activity and Uses Thereof For recombinant production of AG007, AG008, AG009, AG010, or AG011 activity in a host organism, a nucleotide sequence encoding a protein having AG007, AG008, AG009, AG010, or AG011 activity is inserted into an expression cassette designed for the chosen host and introduced into the host where it is recombinantly produced. For example, SEQ ID NO:1, SEQ ID NO:3, SEQ ID NO:5, SEQ ID NO:7, or SEQ ID NO:9, or nucleotide sequences substantially similar to SEQ ID NO:1, SEQ ID NO:3, SEQ ID NO:5, SEQ ID NO:7, or SEQ ID NO:9, or homologs of the AG007, AG008, AG009, AG010, or AG011 coding sequence can be used for the recombinant production of a protein having AG007, AG008, AG009, AG010, or AG011 activity. The choice of specific regulatory sequences such as promoter, signal sequence, 5' and 3' untranslated sequences, and enhancer appropriate for the chosen host is within the level of skill of the routineer in the art. The resultant molecule, containing the individual elements operably linked in proper reading frame, may be inserted into a vector capable of being transformed into the host cell. Suitable expression vectors and methods for recombinant production of proteins are well known for host organisms such as *E. coli*, yeast, and insect cells (see, e.g., Luckow and Summers, *Bio/Technol.* 6: 47 (1988), and baculovirus expression vectors, e.g., those derived from the genome of *Autographica californica* nuclear polyhedrosis virus (AcMNPV). A preferred baculovirus/insect system is pAcHLT (Pharmingen, San Diego, Calif.) used to transfect *Spodoptera frugiperda* Sf9 cells (ATCC) in the presence of linear *Autographa californica* baculovirus DNA (Pharmigen, San Diego, Calif.). The resulting virus is used to infect HighFive *Tricoplusia ni* cells (Invitrogen, La Jolla, Calif.).

In a preferred embodiment, the nucleotide sequence encoding a protein having AG007, AG008, AG009, AG010, or AG011 activity is derived from an eukaryote, such as a mammal, a fly or a yeast, but is preferably derived from a fungus. In a further preferred embodiment, the nucleotide sequence is identical or substantially similar to the nucleotide sequence set forth in SEQ ID NO:1, SEQ ID NO:3, SEQ ID NO:5, SEQ ID NO:7, or SEQ ID NO:9, or encodes a protein having AG007, AG008, AG009, AG010, or AG011 activity, whose amino acid sequence is identical or substantially similar to the amino acid sequence set forth in SEQ ID NO:2, SEQ ID NO:4, SEQ ID NO:6, SEQ ID NO:8, or SEQ ID NO:10. The nucleotide sequence set forth in SEQ ID NO:1, SEQ ID NO:3, SEQ ID NO:5, SEQ ID NO:7, or SEQ ID NO:9 encodes the *A. gossypii* protein, whose amino acid sequence is set forth in SEQ ID NO:2, SEQ ID NO:4, SEQ ID NO:6, SEQ ID NO:8, or SEQ ID NO:10. In another preferred embodiment, the nucleotide sequence is derived from a prokaryote, preferably a bacteria, e.g. *E. coli*. Recombinantly produced protein having AG007, AG008, AG009, AG010, or AG011 activity is isolated and purified using a variety of standard techniques. The actual techniques that may be used will vary depending upon the host organism used, whether the protein is designed for secretion, and other such factors familiar to the skilled artisan (see, e.g. chapter 16 of Ausubel, F. et al., "Current Protocols in Molecular Biology", pub. by John Wiley & Sons, Inc. (1994).

IV. Assays for Characterizing the AG007, AG008, AG009, AG010, and AG011 Proteins Recombinantly produced AG007, AG008, AG009, AG010, and AG011 proteins are useful for a variety of purposes. For example, they can be used in vitro assays to screen for known fungicidal chemicals, whose target has not been identified, to determine if they inhibit AG007, AG008, AG009, AG010, or AG011. Such in vitro assays may also be used as more general screens to identify chemicals that inhibit such enzymatic activities and that are therefore novel fungicide candidates. Alternatively, recombinantly produced AG007, AG008, AG009, AG010, or AG011 proteins are used to elucidate the complex structure of these molecules and to further characterize their association with known inhibitors in order to rationally design new inhibitory fungicides. Nucleotide sequences substantially similar to SEQ ID NO:1, SEQ ID NO:3, SEQ ID NO:5, SEQ ID NO:7, or SEQ ID NO:9, and proteins substantially similar to SEQ ID NO:2, SEQ ID NO:4, SEQ ID NO:6, SEQ ID NO: 8, or SEQ ID NO:10, from any source, including microbial sources, can be used in the assays exemplified herein. Desirably such nucleotide sequences and proteins are derived from fungi. More desirably, they are derived from filamentous fungi, particularly *Ashbya gossypii*. Alternatively, such nucleotide sequences and proteins are derived from non-yeast sources, alternatively from non-*Saccharomyces cerevisiae* sources.

A simple assay is developed to screen for compounds that affect normal functioning of the fungal-encoded activity. Such compounds are promising in vitro leads that can be tested for in vivo fungicidal activity. A nucleic acid sequence of the invention according to any one of the sequences SEQ ID NO:1, SEQ ID NO:3, SEQ ID NO:5, SEQ ID NO:7, or SEQ ID NO:9 is operably linked to a strong inducible promoter, such promoters being known in the art. The vector comprising the selected gene of the invention operably linked to the selected inducible promoter is transformed into bacteria, such as *E. coli*. Transformed *E. coli* harboring and functionally overexpressing an AG007, AG008, AG009, AG010 or AG011 gene are grown in a 96-well format for automated high-throughput screening where inducible over expression of the selected gene is lethal or suppresses growth of the host. Compounds that are effective in blocking function of the AG007, AG008, AG009, AG010, or AG011 protein result in bacterial growth. This growth is measured by simple turbidometric means.

In another embodiment, an assay for inhibitors of the AG007, AG008, AG009, AG010, or AG011 activities uses transgenic fungi or fungal cells capable of overexpressing a nucleotide sequence having AG007, AG008, AG009, AG010, or AG011 activity, respectively, operably linked to a strong inducible promoter, e.g., wherein the selected gene product is enzymatically active in the transgenic fungi and/or fungal cells, and inducible overexpression of the gene inhibits and/or suppresses growth and/or development of the fungus. The nucleotide sequence is preferably derived from an eukaryote, such as a yeast, but is preferably derived from a fungus and more particularly from a filamentous fungus. In a further preferred embodiment, the nucleic acid sequences set forth in SEQ ID NO:1, SEQ ID NO:3, SEQ ID NO:5, SEQ ID NO:7, or SEQ ID NO:9 encode enzymes having AG007, AG008, AG009, AG010, or AG011 activity, respectively, whose amino acid sequence is identical or substantially similar to the amino acid sequence set forth in SEQ ID NO:2, SEQ ID NO:4, SEQ ID NO:6, SEQ ID NO:8, or SEQ ID NO:10. The transgenic fungus or fungal cells are grown in 96-well format microtiter dishes for high-throughput screening. Compounds that are effective in blocking function of the AG007, AG008, AG009, AG010, or AG011 protein results in fungal growth. This growth is measured by methods known in the art. In a particular embodiment, the transgenic fungus is *Ashbya gossypii*.

Similar assays, based on expression of the fungal genes of the invention in yeast, using appropriate expression systems, as described above, may also be used.

In Vitro Inhibitor Assays: Discovery of Small Molecule Ligand that Interacts with the Gene Product of SEQ ID NO:1, SEQ ID NO:3, SEQ ID NO:5, SEQ ID NO:7, or SEQ ID NO:9

Once a protein has been identified as a potential fungicide target, the next step is to develop an assay that allows screening large number of chemicals to determine which ones interact with the protein. Although it is straightforward to develop assays for proteins of known function, developing assays with proteins of unknown functions is more difficult.

This difficulty can be overcome by using technologies that can detect interactions between a protein and a compound without knowing the biological function of the protein. A short description of three methods is presented, including fluorescence correlation spectroscopy, surface-enhanced laser desorption/ionization, and biacore technologies.

Fluorescence Correlation Spectroscopy (FCS) theory was developed in 1972 but it is only in recent years that the technology to perform FCS became available (Madge et al. (1972) Phys. Rev. Lett., 29: 705–708; Maiti et al. (1997) Proc. Natl. Acad. Sci. USA, 94: 11753–11757). FCS measures the average diffusion rate of a fluorescent molecule within a small sample volume. The sample size can be as low as $10^3$ fluorescent molecules and the sample volume as low as the cytoplasm of a single bacterium. The diffusion rate is a function of the mass of the molecule and decreases as the mass increases. FCS can therefore be applied to protein-ligand interaction analysis by measuring the change in mass and therefore in diffusion rate of a molecule upon binding. In a typical experiment, the target to be analysed is expressed as a recombinant protein with a sequence tag, such as a poly-histidine sequence, inserted at the N or C-termninus. The expression takes place in either *E. coli*, yeast or insect cells. The protein is purified by chromatography. For example, the poly-histidine tag can be used to bind the expressed protein to a metal chelate column such as Ni2+ chelated on iminodiacetic acid agarose. The protein is then labelled with a fluorescent tag such as carboxytetramethylrhodamine or BODIPY® (Molecular Probes, Eugene, Oreg.). The protein is then exposed in solution to the potential ligand, and its diffusion rate is determined by FCS using instrumentation available from Carl Zeiss, Inc.

(Thomwood, N.Y.). Ligand binding is determined by changes in the diffusion rate of the protein.

Surface-Enhanced Laser Desorption/Ionization (SELDI) was invented by Hutchens and Yip during the late 1980's (Hutchens and Yip (1993) Rapid Commun. Mass Spectrom. 7: 576–580). When coupled to a time-of-flight mass spectrometer (TOF), SELDI provides a mean to rapidly analyze molecules retained on a chip. It can be applied to ligand-protein interaction analysis by covalently binding the target protein on the chip and analyze by MS the small molecules that bind to this protein (Worrall et al. (1998) Anal. Biochem. 70: 750–756). In a typical experiment, the target to be analysed is expressed as described for FCS. The purified protein is then used in the assay without further preparation. It is bound to the SELDI chip either by utilizing the poly-histidine tag or by other interaction such as ion exchange or hydrophobic interaction. The chip thus prepared is then exposed to the potential ligand via, for example, a delivery system capable to pipet the ligands in a sequential manner (autosampler). The chip is then submitted to washes of increasing stringency, for example a series of washes with buffer solutions containing an increasing ionic strength. After each wash, the bound material is analysed by submitting the chip to SELDI-TOF. Ligands that specifically bind the target will be identified by the stringency of the wash needed to elute them.

Biacore relies on changes in the refractive index at the surface layer upon binding of a ligand to a protein immobilized on the layer. In this system, a collection of small ligands is injected sequentially in a 2–5 ul cell with the immobilized protein. Binding is detected by surface plasmon resonance (SPR) by recording laser light refracting from the surface. In general, the refractive index change for a given change of mass concentration at the surface layer, is practically the same for all proteins and peptides, allowing a single method to be applicable for any protein (Liedberg et al. (1983) Sensors Actuators 4: 299–304; Malmquist (1993) Nature, 361: 186–187). In a typical experiment, the target to be analysed is expressed as described for FCS. The purified protein is then used in the assay without further preparation. It is bound to the Biacore chip either by utilizing the poly-histidine tag or by other interaction such as ion exchange or hydrophobic interaction. The chip thus prepared is then exposed to the potential ligand via the delivery system incorporated in the instruments sold by Biacore (Uppsala, Sweden) to pipet the ligands in a sequential manner (autosampler). The SPR signal on the chip is recorded and changes in the refractive index indicate an interaction between the immobilized target and the ligand. Analysis of the signal kinetics on rate and off rate allows the discrimination between non-specific and specific interaction.

V. In Vivo Inhibitor Assay

In one embodiment, a suspected fungicide, for example identified by in vitro screening, is applied to fungi at various concentrations. After application of the suspected fungicide, its effect on the fungus, for example inhibition or suppression of growth and development is recorded.

VI. Generating Derivatives of AG007, AG008, AG009, AG010, AG011 Proteins

Fungicide resistant AG007, AG008, AG009, AG010, and AG011 proteins are also obtained using methods involving in vitro recombination, also called DNA shuffling. By DNA shuffling, mutations, preferably random mutations, are introduced into nucleotide sequences encoding AG007, AG008, AG009, AG010, or AG011 activity. DNA shuffling also leads to the recombination and rearrangement of sequences within a AG007, AG008, AG009, AG010, or AG011 gene or to recombination and exchange of sequences between two or more different of AG007, AG008, AG009, AG010, or AG011 genes. These methods allow for the production of millions of mutated AG007, AG008, AG009, AG010, or AG011 coding sequences. The mutated genes, or shuffled genes, are screened for desirable properties, e.g. improved tolerance to fungicides and for mutations that provide broad spectrum tolerance to the different classes of inhibitor chemistry. Such screens are well within the skills of a routineer in the art.

In a preferred embodiment, a mutagenized AG007, AG008, AG009, AG010 or AG011 gene is formed from at least one template AG007, AG008, AG009, AG010, or AG011 gene, wherein the template AG007, AG008, AG009, AG010, or AG011 gene has been cleaved into double-stranded random fragments of a desired size, and comprising the steps of adding to the resultant population of double-stranded random fragments one or more single or double-stranded oligonucleotides, wherein said oligonucleotides comprise an area of identity and an area of heterology to the double-stranded random fragments; denaturing the resultant mixture of double-stranded random fragments and oligonucleotides into single-stranded fragments; incubating the resultant population of single-stranded fragments with a polymerase under conditions which result in the annealing of said single-stranded fragments at said areas of identity to form pairs of annealed fragments, said areas of identity being sufficient for one member of a pair to prime replication of the other, thereby forming a mutagenized double-stranded polynucleotide; and repeating the second and third steps for at least two further cycles, wherein the resultant mixture in the second step of a further cycle includes the mutagenized double-stranded polynucleotide from the third step of the previous cycle, and the further cycle forms a further mutagenized double-stranded polynucleotide, wherein the mutagenized polynucleotide is a mutated AG007, AG008, AG009, AG010, or AF011 gene having enhanced tolerance to a fungicide which inhibits naturally occurring AG007, AG008, AG009, AG010, or AG011 activity. In a preferred embodiment, the concentration of a single species of double-stranded random fragment in the population of double-stranded random fragments is less than 1% by weight of the total DNA. In a further preferred embodiment, the template double-stranded polynucleotide comprises at least about 100 species of polynucleotides. In another preferred embodiment, the size of the double-stranded random fragments is from about 5 bp to 5 kb. In a further preferred embodiment, the fourth step of the method comprises repeating the second and the third steps for at least 10 cycles. Such method is described e.g. in Stemmer et al. (1994) Nature 370: 389–391, in U.S. Pat. No. 5,605,793, U.S. Pat. No. 5,811,238 and in Crameri et al. (1998) Nature 391: 288–291, as well as in WO 97/20078, and these references are incorporated herein by reference.

In another preferred embodiment, any combination of two or more different AG007, AG008, AG009, AG010, or AG011 genes are mutagenized in vitro by a staggered extension process (StEP), as described e.g. in Zhao et al. (1998) Nature Biotechnology 16: 258–261. The two or more AG007, AG008, AG009, AG010, or AG011 genes are used as template for PCR amplification with the extension cycles of the PCR reaction preferably carried out at a lower temperature than the optimal polymerization temperature of the polymerase. For example, when a thermostable polymerase with an optimal temperature of approximately 72° C. is used, the temperature for the extension reaction is desirably below 72° C., more desirably below 65° C., preferably below 60° C., more preferably the temperature for the extension reaction is 55° C. Additionally, the duration of the extension reaction of the PCR cycles is desirably shorter than usually carried out in the art, more desirably it is less than 30 seconds, preferably it is less than 15 seconds, more preferably the duration of the extension reaction is 5 seconds. Only a short DNA fragment is polymerized in each extension reaction, allowing template switch of the extension products between the starting DNA molecules after each cycle of denaturation and annealing, thereby generating diversity among the extension products. The optimal number of cycles in the PCR reaction depends on the length of the AG007, AG008, AG009, AG010, or AG011 genes to be mutagenized but desirably over 40 cycles, more desirably over 60 cycles, preferably over 80 cycles are used. Optimal extension conditions and the optimal number of PCR cycles for every combination of AG007, AG008, AG009, AG010, or AG011 genes are determined as described in using procedures well-known in the art. The other parameters for the PCR reaction are essentially the same as commonly used in the art. The primers for the amplification reaction are preferably designed to anneal to DNA sequences located outside of the AG007, AG008, AG009, AG010, or AG011 genes, e.g. to DNA sequences of a vector comprising the AG007, AG008, AG009, AG010, or AG011 genes, whereby the different AG007, AG008, AG009, AG010, or AG011 genes used in the PCR reaction are preferably comprised in separate vectors. The primers desirably anneal to sequences located less than 500 bp away from AG007, AG008, AG009, AG010, or AG011 sequences, preferably less than 200 bp away from the AG007, AG008, AG009, AG010, or AG011 sequences, more preferably less than 120 bp away from the AG007, AG008, AG009, AG010, or AG011 sequences. Preferably, the AG007, AG008, AG009, AG010, or AG011 sequences are surrounded by restriction sites, which are included in the DNA sequence amplified during the PCR reaction, thereby facilitating the cloning of the amplified products into a suitable vector. In another preferred embodiment, fragments of AG007, AG008, AG009, AG010, or AG011 genes having cohesive ends are produced as described in WO 98/05765. The cohesive ends are produced by ligating a first oligonucleotide corresponding to a part of a AG007, AG008, AG009, AG010, or AG011 gene to a second oligonucleotide not present in the gene or corresponding to a part of the gene not adjoining to the part of the gene corresponding to the first oligonucleotide, wherein the second oligonucleotide contains at least one ribonucleotide. A double-stranded DNA is produced using the first oligonucleotide as template and the second oligonucleotide as primer. The ribonucleotide is cleaved and removed. The nucleotide(s) located 5' to the ribonucleotide is also removed, resulting in double-stranded fragments having cohesive ends. Such fragments are randomly reassembled by ligation to obtain novel combinations of gene sequences.

Any AG007, AG008, AG009, AG010, or AG011 gene or any combination of AG007, AG008, AG009, AG010, or AG001 genes, or homologs thereof, is used for in vitro recombination in the context of the present invention, for example, a AG007, AG008, AG009, AG010, or AG011 gene derived from a fungus, such as, e.g.*Ashbya gossypii*, e.g. a AG007, AG008, AG009, AG010 or AG011 gene set forth in SEQ ID NO:1, SEQ ID NO:3, SEQ ID NO:5, SEQ ID NO:7 or SEQ ID NO:9. Whole AG007, AG008, AG009, AG010 or AG011 genes or portions thereof are used in the context of the present invention. The library of mutated AG007, AG008, AG009, AG010, or AG011 genes obtained by the methods described above are cloned into appropriate expression vectors and the resulting vectors are transformed into an appropriate host, for example a fungal cell, an algae like Chlamydomonas, a yeast or a bacteria. An appropriate host requires AG007, AG008, AG009, AG010, or AG011 gene product activity for growth. Host cells transformed with the vectors comprising the library of mutated AG007, AG008, AG009, AG010, or AG011 genes are cultured on medium that contains inhibitory concentrations of the inhibitor and those colonies that grow in the presence of the inhibitor are selected. Colonies that grow in the presence of normally inhibitory concentrations of inhibitor are picked and purified by repeated restreaking. Their plasmids are purified and the DNA sequences of cDNA inserts from plasmids that pass this test are then determined.

An assay for identifying a modified AG007, AG008, AG009, AG010, or AG011 gene that is tolerant to an inhibitor may be performed in the same manner as the assay to identify inhibitors of the AG007, AG008, AG009, AG010, or AG011 activity (Inhibitor Assay, above) with the following modifications: First, a mutant AG007, AG008, AG009, AG010, or AG011 protein is substituted in one of the reaction mixtures for the wild-type AG007, AG008, AG009, AG010, or AG011 protein of the inhibitor assay. Second, an inhibitor of wild-type enzyme is present in both reaction mixtures. Third, mutated activity (activity in the to presence of inhibitor and mutated enzyme) and unmutated activity (activity in the presence of inhibitor and wild-type enzyme) are compared to determine whether a significant increase in enzymatic activity is observed in the mutated activity when compared to the unmutated activity. Mutated activity is any measure of activity of the mutated enzyme while in the presence of a suitable substrate and the inhibitor. Unmutated activity is any measure of activity of the wild-type enzyme while in the presence of a suitable substrate and the inhibitor.

VII. Method of Using Genes to Distinguish Fungal Species

In a further embodiment according to the invention, a DNA sequence selected from the Sequence Listing may also be used for distinguishing among different species of plant pathogenic fungi and for distinguishing fungal pathogens from other pathogens such as bacteria (Weising et al. (1995) In "DNA Fingerprinting in Plants and Fungi", CRC Press, Boca Raton, pp. 157–227).

VIII. Fungal Transformation Technology

An AG007, AG008, AG009, AG010, or AG011 gene, or homologs thereof, can be incorporated in fungal or bacterial cells using conventional recombinant DNA technology. Generally, this involves inserting a DNA molecule encoding the AG007, AG008, AG009, AG010, or AG011 gene into an expression system to which the DNA molecule is heterologous (i.e., not normally present) using standard cloning procedures known in the art. The vector contains the necessary elements for the transcription and translation of the inserted protein-coding sequences in a fungal cell containing the vector. A large number of vector systems known in the art can be used, such as plasmids (van den Hondel and Punt (1990) In "Applied Molecular Genetics of Fungi," Peberdy, Catten, Ogden, Bennett (eds), Cambridge University Press, New York, pp. 1–28). The components of the expression system may also be modified to increase expression. For example, truncated sequences, nucleotide substitutions, nucleotide optimization or other modifications may be employed. Expression systems known in the art can be used to transform fingal cells under suitable conditions (Lemnke and Peng (1997) In "The Mycota", Vol. 11 Kuck (ed), Springer-Verlag, Berlin, pp. 109–139). A heterologous DNA sequence comprising an AG007, AG008, AG009, AG010, or AG011 gene is preferably stably transformed and integrated into the genome of the fungal host cells.

Gene sequences intended for expression in transgenic fungi are first assembled in expression cassettes behind a suitable promoter expressible in fungi (Lang-Hinrichs (1997) In "The Mycota:, Vol II Kuck (ed), Springer-Verlag, Berlin, pp. 141–153; Jacobs and Stahl (1997) In "The Mycota", Vol II Kuck (ed), Springer-Verlag, Berlin, pp. 155–167). The expression cassettes may also comprise any further sequences required or selected for the expression of the heterologous DNA sequence. Such sequences include, but are not restricted to, transcription terminators, extraneous sequences to enhance expression such as introns, and sequences intended for the targeting of the gene product to specific organelles and cell compartments. These expression cassettes can then be easily transferred to the fungal transformation vectors as described (Lemke and Peng (1997) In "The Mycota", Vol II Kuck (ed), Springer-Verlag, Berlin, pp. 109–139).

EXAMPLES

Standard recombinant DNA and molecular cloning techniques used here are well known in the art and are described by Sambrook, et al., *Molecular Cloning*, eds., Cold Spring Harbor Laboratory Press, Cold Spring Harbor, N.Y. (1989) and by T. J. Silhavy, M. L. Berman, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

Construction and Characterization of a Genomic Library of *A. gossypii* (strain ATCC10895), identification of ORFs and promoters is described in U.S. patent application Ser. No.: 008/998,416 which is hereby incorporated by reference in its entirety.

Example 1

Identification of Antifungal Drug Targets Represented in the Sequence Listing Gene disruptions of *A. gossypii* genes are generated by a method using short flanking homology regions to produce gene targeting events. The short flanking homology regions are included within polymerase chain reaction primers of 65 nucleotide overall sequence length. Each of these 65-mers contains approximately 45 nucleotides homology to the target gene locus the target gene locus being identified as described in U.S. patent application Ser. No. 5 08/998,416 incorporated above by reference, and 20 nucleotides homology (invariant) to a geneticin resistance gene module also described in U.S. patent application Ser. No. 008/998,416 previously incorporated by reference), with one primer (designated S1) anchored to the 5' end of the geneticin resistance module (using the invariant sequence 5'-GCTAGGGATAACAGGGTAAT-3') (SEQ ID NO:11) and the other primer of the pair (designated S2) anchored to the 3' end of the geneticin resistance module (using the invariant sequence 5'-AGGCATGCAAGCTTAGATCT-3') (SEQ ID NO:12). The PCR product resulting from the amplification of the geneticin resistance module with such an S1/S2 primer pair thus consists of the module flanked by short flanking homology regions of ca. 45 nucleotides specific to the chosen gene disruption site.

Once an S1/S2 primer pair is designed for a particular gene target, approximately 10 ug of the desired geneticin resistance module is obtained by linearizing a vector containing the geneticin resistance gene positioned behind the an appropriate fungal promoter (for example, the *Saccharomyces cerevisiae* TEF1 promoter) and subjecting the linearized template to approximately 35 rounds of a PCR reaction consisting of the following steps:

Step 1: Denaturation at 96 C for 30 seconds;
Step 2: Primer annealing at 50 C for 30 seconds;
Step 3: Elongation reaction at 72 C for 2.5 minutes. Following the 35th round of this protocol, a final elongation period of 5 minutes at 72 C is carried out.

Transformation of the PCR product resulting from amplification with the S1/S2 primer pair is done by electroporation as follows:

1) Inoculate 100 ml of AFM media (1% casein peptone, 2% glucose, 1% yeast extract, 0.1% myo-inositol) with an Ashbya spore suspension of approximately $10^7$ spores.
2) Incubate at 30 C for a maximum of 18 hours at a shaker speed of 200 rpm.
3) Collect the resultant fungal mycelia by filtration and wash once with sterile water.
4) Resuspend 1 gram of mycelia (wet weight) in 40 ml of 50 mM potassium phosphate buffer, pH 7.5 containing 25mM DTT and incubate at 30 C for 30 minutes with gentle shaking.
5) Collect the mycelia by filtration and wash once with 50 ml of cold STM buffer (275 mM sucrose, 10 mM Tris-HCl, pH 7.5, 2 mM $MgCl_2$).
6) Resuspend the mycelia to a dense mixture in STM buffer.
7) Mix approximately 150 ul of the mycelial mixture with 10 ug of PCR product (in a maximum volume of 50 ul) in an Eppendorf tube and transfer the mixture to an electroporation cuvette with a 4mM gap distance.
8) Apply an electric field pulse of 1.5 kV, 100 ohms, 25 uF which will result in a pulse length of approximately 2.3 milliseconds. Add 1 ml of AFM media to the cuvette and spread equal amounts onto 3 pre-dried AFM agar plates.
9) Incubate plates for a minimum of 4 hours at 30 C.
10) Overlay the plates with 8 ml of a 0.5% agarose toplayer containing Geneticin/G418 at a final concentration of 200 ug/ml.
11) Incubate at 30 C for approximately 3 days to allow sufficient growth of geneticin resistant transformants.

Verification of the desired transformation event resulting in homologous integration of the geneticin resistance module in the target of interest is achieved by PCR using verification primers designated G1 (positioned upstream of the S1 region) and G4 (positioned downstream of the S2 region) and template DNA purified from putative Ashbya transformants. Additional verification primers designated G2 (5'-GTTTAGTCTGACCATCTCATCTG-3') (SEQ ID NO:13) and G3 (5'-TCGCAGACCGATACCAGGATC-3') (SEQ ID NO:14) are derived from the open reading frame of the selectable geneticin resistance gene such that the detection of a G1/G2 PCR product and or a G3/G4 PCR product of a predictable size serves to verify the desired gene disruption event. Also, verification of the desired gene disruption can be determined by standard DNA hybridization experiments.

Determination of whether a gene is essential to growth of Ashbya can be achieved by the following analysis. The transformation of DNA fragments described above utilizes multinucleate Ashbya mycelia as recipients. Therefore a primary transformant able to grow on geneticin containing media originates as a mycelium containing cells at least one of which has at least one transformed nucleus, but usually containing non-transformed nuclei as well. Thus, if an essential gene is disrupted in the transformed nucleus, the essential gene product can, in many instances, still be supplied by the non-transformed nuclei within the same cell. Such primary transformants usually exhibit normal growth and sporulation, and spores are collected from primary transformants allowed to grow at 30 C for at least 5 days. Since spores are uninucleate, however, transfornants which have an essential gene disrupted in nuclei containing the geneticin resistance cartridge will fail to yield spores which grow normally, if at all, on geneticin-containing media.

S1 and S2 primer pairs usable to generate disruptions of the indicated genes are as follows:
AG007: S1: 5'-ATATGTACTTCGAGAGACGTCCAGA-GCTACTGAGCAAATCCACACGCTAGGGATAACAG-GGTAAT-3' (SEQ ID NO:15)
AG007: S2: 5'-TCTTCATAGCGTATATTTTACCGGTAT-CTTTCTTCTGCACCAGAAGGCATGCAACTTAGAT-CT-3' (SEQ ID NO:16)
AG008: S1: 5'-GTATTGGCAAACGGGTGTTCGACAA-GTGCGCGGAGTGGCTGCCGCTGGCGCTGGGATAA-CAGGGTAAT-3' (SEQ ID NO:17)
AG008: S2: 5'-GTGACGGGGATGCAGGCGGCGGCG-CAGGCTCCAACCTCGCGGGATTCTCAGGCATGCA-AGCTTAGATCT-3' (SEQ ID NO:18)
AG009:S1: 5'-GCTACGCCCCGCAGGTGTTCGTGTTC-CGCAACCTGGAGTCGGGGCAGGTGGCTAGGGATA-ACAGGGTAAT-3' (SEQ ID NO:19)
AG009: S2: 5'-CCATGCGCGGCAGGAACTGGTGCTG-GACGGCGGGCAGCGCGGCCCAGTGCAGGCATGCA-AGCTTAGATCT-3' (SEQ ID NO:20)
AG010: S1: 5'-TGTCGCTGGTGAGGCTTAAGAAGGG-GAAGAAGCGGTTCGAAGTTGCTTGCGCTAGGGAT-AACAGGGTAAT-3' (SEQ ID NO:21)
AG010: S2: 5'-CAGAGCGTGACCAGTTCGCGGTAGT-TCATTGGGTCGATCAGGCCTGTGCAGGCATGCAA-GCTTAGATCT-3' (SEQ ID NO:22)
AG011: S1: 5'-CGGACGCACAGTAAACAGGTTGCTA-GAGACTTGCTAGAGAATTAGGCTAGGGATAACAG-GGTAAT-3' (SEQ ID NO:23)
AG011: S2: 5'-ATCTATCCTGATCTCACAAATATTAAT-TTTATCCATGAAATTAACAGGCATGCAAGCTTAGA-TCT-3' (SEQ ID NO:24)

Example 2

Expression of Recombinant AG007, AG008, AG009 AG010, or AG011 Protein in Heterologous Expression Systems The coding region of the protein, corresponding to SEQ ID NO:1, SEQ ID NO:3, SEQ ID NO:5, SEQ ID NO:7, or SEQ ID NO:9 is subcloned into previously described expression vectors, and transformed into *E. coli* using the manufacturer's conditions. Specific examples include plasmids such as pBluescript (Stratagene, La Jolla, Calif.), the pET vector system (Novagen, Inc., Madison, Wis.) pFLAG (International Biotechnologies, Inc., New Haven, Conn.), and pTrcHis (Invitrogen, La Jolla, Calif.). *E. coli* is cultured, and expression of the AG007, AG008, AG009 or AG010 activity is confirmed. Alternatively, eukaryotic expression systems such as cultured insect cells infected with specific viruses may be preferred. Examples of vectors and insect cell lines are described previously. Protein conferring AG007, AG008, AG009, AG010, or AG011 activity is isolated using standard techniques.

Example 3

In vitro Recombination of AG007, AG008, AG009, AG010, or AG011 Genes by DNA Shuffling The nucleotide sequence of SEQ ID NO:1, SEQ ID NO:3, SEQ ID NO:5, SEQ ID NO:7, or SEQ ID NO:9 is amplified by PCR. The resulting DNA fragment is digested by DNaseI treatment essentially as described (Stemmer et al. (1994) PNAS 91: 10747–10751) and the PCR primers are removed from the reaction mixture. A PCR reaction is carried out without primers and is followed by a PCR reaction with the primers, both as described (Stemmer et al. (1994) PNAS 91: 10747–10751). The resulting DNA fragments are cloned into pTRC99a (Pharmacia, Cat no: 27-5007-01) for use in bacteria, and transformed into a bacterial strain deficient in AG007, AG008, AG009, AG010, or AG011 activity by electroporation using the Biorad Gene Pulser and the manufacturer's conditions. The transformed bacteria are grown on medium that contains inhibitory concentrations of an inhibitor of AG007, AG008, AG009, AG010, or AG011 activity and those colonies that grow in the presence of the inhibitor are selected. Colonies that grow in the presence of normally inhibitory concentrations of inhibitor are picked and purified by repeated restreaking. Their plasmids are purified and the DNA sequences of cDNA inserts from plasmids that pass this test are then determined. Alternatively, the DNA fragments are cloned into expression vectors for transient or stable transformation into fungal cells, which are screened for differential survival and/or growth in the presence of an inhibitor of AG007, AG008, AG009, AG010, or AG011 activity. In a similar reaction, PCR-amplified DNA fragments comprising the Ashbya AG007, AG008, AG009, AG010, or AG011 gene encoding the protein and PCR-amplified DNA fragments derived from or comprising another AG007, AG008, AG009, AG010, or AG001 gene are recombined in vitro and resulting variants with improved tolerance to the inhibitor are recovered as described above.

Example 4

In vitro Recombination of AG007, AG008, AG009, AG010, or AG011 Genes by Staggered Extension Process The Ashbya AG007, AG008, AG009, AG010, or AG011 gene encoding the AG007, AG008, AG009, AG010, or AG011 protein and another AG007, AG008, AG009, AG010, or AG011 gene, or homologs thereof, or fragments thereof, are each cloned into the polylinker of a pBluescript vector. A PCR reaction is carried out essentially as described (Zhao et al. (1998) Nature Biotechnology 16: 258–261) using the "reverse primer" and the "M13–20 primer" (Stratagene Catalog). Amplified PCR fragments are digested with appropriate restriction enzymes and cloned into pTRC99a and mutated AG007, AG008, AG009, AG010, or AG011 genes are screened as described in Example 3.

Example 5

In vitro Binding Assays

Recombinant AG007, AG008, AG009, AG010, or AF011 protein is obtained, for example, according to Example 2. The protein is immobilized on chips appropriate for ligand binding assays using techniques which are well known in the art. The protein immobilized on the chip is exposed to sample compound in solution according to methods well know in the art. While the sample compound is in contact with the immobilized protein measurements capable of detecting protein-ligand interactions are conducted. Examples of such measurements are SELDI, biacore and FCS, described above. Compounds found to bind the protein are readily discovered in this fashion and are subjected to further characterization.

Example 6

Cell-Based Assay

Simple cell-based assays are developed to screen for compounds that affect normal functioning of the specific fungal-encoded activity. Such compounds are promising in vitro leads that can be tested for in vivo fungicidal activity. A nucleic acid sequence of the invention according to any one of the sequences SEQ ID NO:1, SEQ ID NO:3, SEQ ID NO: 5, SEQ ID NO:7, or SEQ ID NO:9 is operably linked to a strong inducible promoter, e.g. GAL1 promoter, GAL10 promoter, or other such promoters known in the art. In one embodiment, overexpression of the essential fungal gene confers upon the fungal cells a greater degree of resistance to an inhibitory compound than is attainable in the wild type fungus. Wild type fungal cells are cultured in 96 well microtiter plates (e.g. 100 ul volume per well) in the presence of a defined concentration of a different chemical compound in each well. Likewise, transgenic fungal cells overexpressing the essential fungal gene (i.e. under inducing conditions) are challenged with the same set of chemical compounds at the same defined concentration. Situations in which growth of the wild type fungus, but not the transgenic fungus, is inhibited by a given compound are identified as prospective situations in which overexpression of the particular gene confers resistance to the inhibitory effect of the test compound. Follow up experiments are carried out to repeat this result with a variety of concentrations of the identified compounds.

In another embodiment, induced overexpression of the essential fungal gene has deleterious effects upon growth or viability of the fungal cells. In this instance, transgenic fungal cells in which the essential fungal gene is operably linked to an inducible promoter are cultured in 96 well microtiter plates in the presence of a defined concentration of a different chemical test compound in each well. After a short incubation period, cells are shifted to full inducing conditions (for example by adding an inducing compound to each well). Normally this induced overexpression would lead to growth arrest of the culture, but, in wells containing inhibitors of the essential fungal gene, growth would proceed and would be monitored via the increased turbidity within such wells.

The above disclosed embodiments are illustrative. This disclosure of the invention will place one skilled in the art in possession of many variations of the invention. All such obvious and foreseeable variations are intended to be encompassed by the appended claims.

What is claimed is:

1. An isolated nucleotide sequence consisting essentially of SEQ ID NO:1.

2. The nucleotide sequence of claim 1, wherein the nucleotide sequence is a fungal nucleotide sequence.

3. The nucleotide sequence of claim 2, wherein the fungus is *Ashbya gossypii*.

4. A chimeric gene comprising a promoter operably linked to a nucleotide sequence according to claim 1.

5. The chimeric gene of claim 4 wherein the promoter is an inducible promoter.

6. A recombinant vector comprising a chimeric gene according to claim 4 wherein said vector is capable of being stably transformed into a host cell.

7. A host cell comprising the vector according to claim 6, wherein the nucleotide sequence is expressible in the host cell.

8. The host cell according to claim 7, wherein the host cell is eukaryotic.

9. The host cell according to claim 7, wherein the host cell is selected from the group consisting of a yeast cell and a fungal cell.

10. The host cell according to claim 9, wherein the host cell is a filamentous fungal cell.

11. The host cell according to claim 10, wherein the host cell is an *Ashbya gossypii* cell.

12. The host cell according to claim 7 wherein the host cell is a prokaryotic cell.

13. The host cell according to claim 12 wherein the host cell is a bacterial cell.

14. The nucleotide sequence of claim 1, wherein the nucleotide sequence is SEQ ID NO:1.

15. The nucleotide sequence of claim 1, wherein the nucleotide sequence encodes an amino acid sequence consisting essentially of SEQ ID NO:2.

16. An isolated nucleotide sequence encoding an amino acid sequence according to SEQ ID NO:2.

* * * * *

SEQUENCE LISTING

```
<160> NUMBER OF SEQ ID NOS: 24

<210> SEQ ID NO 1
<211> LENGTH: 2160
<212> TYPE: DNA
<213> ORGANISM: Ashbya gossypii
<220> FEATURE:
<221> NAME/KEY: CDS
<222> LOCATION: (1)..(2160)

<400> SEQUENCE: 1 atg ttc gga cag ggt tat tac cag ggc aat cgc gac cag gac tcg ccg      48
Met Phe Gly Gln Gly Tyr Tyr Gln Gly Asn Arg Asp Gln Asp Ser Pro
  1               5                  10                  15 ctg cag cgg ccg ccg gcc gcg cag ttc agc agt gca tac atg gag cag      96
Leu Gln Arg Pro Pro Ala Ala Gln Phe Ser Ser Ala Tyr Met Glu Gln
             20                  25                  30 cag ggc tca cat cag tca ctg cag gag cac ttg gcg tac gag cag ctg     144
Gln Gly Ser His Gln Ser Leu Gln Glu His Leu Ala Tyr Glu Gln Leu
         35                  40                  45 cag ctg cag cag caa cag cag cag cag cag cag cac gct gct gcg cca     192
Gln Leu Gln Gln Gln Gln Gln Gln Gln Gln Gln His Ala Ala Ala Pro
     50                  55                  60 cat gcc aac ggg gat ggt tat ggc gct ggt ttt aca gat atc cct acg     240
His Ala Asn Gly Asp Gly Tyr Gly Ala Gly Phe Thr Asp Ile Pro Thr
 65                  70                  75                  80 atg ctg ggc tcg gta ggt gcg cca tct ccg gcc ttc cag cct cca atg     288
Met Leu Gly Ser Val Gly Ala Pro Ser Pro Ala Phe Gln Pro Pro Met
                 85                  90                  95 gtt gtg ggg atg cag cag cag cca att aac acg ccc ccg cct acg gcg     336
Val Val Gly Met Gln Gln Gln Pro Ile Asn Thr Pro Pro Pro Thr Ala
            100                 105                 110 acc agc att tac agc cag aac aac aac tct ttt acg aac gtg aac gac     384
Thr Ser Ile Tyr Ser Gln Asn Asn Asn Ser Phe Thr Asn Val Asn Asp
        115                 120                 125 act act ctt gcc ccc ggc cat tct tca cca gga cac tac tcc aac agc     432
Thr Thr Leu Ala Pro Gly His Ser Ser Pro Gly His Tyr Ser Asn Ser
    130                 135                 140
```

```
tcg gac tac agt ggg cag cag cct gct tcc tct gcg tat aaa cag ttt        480
Ser Asp Tyr Ser Gly Gln Gln Pro Ala Ser Ser Ala Tyr Lys Gln Phe
145                 150                 155                 160 ggg ggg tcg gag tcc cct tta cag cct gca gct cta cct gga cta cta        528
Gly Gly Ser Glu Ser Pro Leu Gln Pro Ala Ala Leu Pro Gly Leu Leu
                165                 170                 175 gac gga agc ctt ggc gat cag acg cta gtg gga aac cag agc tcg cag        576
Asp Gly Ser Leu Gly Asp Gln Thr Leu Val Gly Asn Gln Ser Ser Gln
        180                 185                 190 ggc gct atg cta tcc cgt cag tcc ctg cag tgc tct tca gtt cca caa        624
Gly Ala Met Leu Ser Arg Gln Ser Leu Gln Cys Ser Ser Val Pro Gln
            195                 200                 205 tcg ccc aat ggg ggc caa cgg caa acc tcg gga gtg ggg aac tat atg        672
Ser Pro Asn Gly Gly Gln Arg Gln Thr Ser Gly Val Gly Asn Tyr Met
210                 215                 220 tac ttc gag aga cgt cca gag cta ctg agc aaa tcc aca caa gaa aaa        720
Tyr Phe Glu Arg Arg Pro Glu Leu Leu Ser Lys Ser Thr Gln Glu Lys
225                 230                 235                 240 gcg gct gca gtg aag ctg aaa gtc gag aat ttc tac caa tca tct gtc        768
Ala Ala Ala Val Lys Leu Lys Val Glu Asn Phe Tyr Gln Ser Ser Val
                245                 250                 255 aat cat gcc att gag cgc aac caa aga cgc gtg gaa ctt gaa tcc cag        816
Asn His Ala Ile Glu Arg Asn Gln Arg Arg Val Glu Leu Glu Ser Gln
        260                 265                 270 cta tta tct cat ggc tgg tct gaa gag aga aag aac aga cag ctt tct        864
Leu Leu Ser His Gly Trp Ser Glu Glu Arg Lys Asn Arg Gln Leu Ser
            275                 280                 285 tca ctg ggt aaa aag gag tcg cag ttt ctg cgc ttg cgt agg aca cgg        912
Ser Leu Gly Lys Lys Glu Ser Gln Phe Leu Arg Leu Arg Arg Thr Arg
290                 295                 300 cta tcc ctg gaa gat ttc cac act gtt aaa gtc ata gga aag ggt gca        960
Leu Ser Leu Glu Asp Phe His Thr Val Lys Val Ile Gly Lys Gly Ala
305                 310                 315                 320 ttc ggt gag gtc cgt ctg gtg cag aag aaa gat acc ggt aaa ata tac       1008
Phe Gly Glu Val Arg Leu Val Gln Lys Lys Asp Thr Gly Lys Ile Tyr
                325                 330                 335 gct atg aag aca ttg tta aaa tca gaa atg tac aag aag gat caa tta       1056
Ala Met Lys Thr Leu Leu Lys Ser Glu Met Tyr Lys Lys Asp Gln Leu
        340                 345                 350 gcc cac gtc aag gcc gag agg gat gtg ttg gcc gga agc gac tct ccg       1104
Ala His Val Lys Ala Glu Arg Asp Val Leu Ala Gly Ser Asp Ser Pro
            355                 360                 365 tgg gtc gtg tcg tta tac tat tct ttc caa gat gcc cag tac cta tac       1152
Trp Val Val Ser Leu Tyr Tyr Ser Phe Gln Asp Ala Gln Tyr Leu Tyr
370                 375                 380 ttg atc atg gaa ttt ttg ccc ggt ggt gac ctg atg acc atg tta atc       1200
Leu Ile Met Glu Phe Leu Pro Gly Gly Asp Leu Met Thr Met Leu Ile
385                 390                 395                 400 agg tgg cag ata ttc acc gag gac gtc acc aga ttc tac atg gcg gag       1248
Arg Trp Gln Ile Phe Thr Glu Asp Val Thr Arg Phe Tyr Met Ala Glu
                405                 410                 415 tgt atc ctg gca att gag gct ata cac aag ctg ggc ttt atc cat aga       1296
Cys Ile Leu Ala Ile Glu Ala Ile His Lys Leu Gly Phe Ile His Arg
        420                 425                 430 gat atc aag ccg gat aac att ctg atc gac atc agg ggt cac atc aaa       1344
Asp Ile Lys Pro Asp Asn Ile Leu Ile Asp Ile Arg Gly His Ile Lys
            435                 440                 445 ctt tcc gac ttc ggt ctg tcg aca ggg ttc cac aaa acg cat gac tcc       1392
Leu Ser Asp Phe Gly Leu Ser Thr Gly Phe His Lys Thr His Asp Ser
450                 455                 460
```

-continued

```
aac tac tac aag aag ctg ctt cag gag gac gag cag cag cag aac ggc    1440
Asn Tyr Tyr Lys Lys Leu Leu Gln Glu Asp Glu Gln Gln Gln Asn Gly
465                 470                 475                 480 ggg aac atg ggc aaa tat ccc gca tcc ggt ggc ggc ggc aac ggc ggc    1488
Gly Asn Met Gly Lys Tyr Pro Ala Ser Gly Gly Gly Gly Asn Gly Gly
                485                 490                 495 ggc aac aga aac acc atg ctt gtc gac gcc atc cac ctg acc atg aca    1536
Gly Asn Arg Asn Thr Met Leu Val Asp Ala Ile His Leu Thr Met Thr
            500                 505                 510 aac agg cag cag atg caa acc tgg cgc aag tcc cgt agg ctc atg gcc    1584
Asn Arg Gln Gln Met Gln Thr Trp Arg Lys Ser Arg Arg Leu Met Ala
        515                 520                 525 tac tcc acc gtc ggt acg cca gac tac atc gcc ccg gag atc ttc ctc    1632
Tyr Ser Thr Val Gly Thr Pro Asp Tyr Ile Ala Pro Glu Ile Phe Leu
    530                 535                 540 tac cag ggc tac ggt cag gag tgc gac tgg tgg tcc ctc ggc gcc atc    1680
Tyr Gln Gly Tyr Gly Gln Glu Cys Asp Trp Trp Ser Leu Gly Ala Ile
545                 550                 555                 560 atg tac gag tgt ctg atc ggg tgg ccg ccg ttc tgc tcg gag acc ccc    1728
Met Tyr Glu Cys Leu Ile Gly Trp Pro Pro Phe Cys Ser Glu Thr Pro
                565                 570                 575 cag gaa acc tac agg aag atc atg aac ttc gag cag acg ctg gtg ttc    1776
Gln Glu Thr Tyr Arg Lys Ile Met Asn Phe Glu Gln Thr Leu Val Phe
            580                 585                 590 cca gac gac atc cac atc tca tac gag gca gag gac ctc atc cgc cgg    1824
Pro Asp Asp Ile His Ile Ser Tyr Glu Ala Glu Asp Leu Ile Arg Arg
        595                 600                 605 ctg ctc tcg cac gcc gac gaa cgg ctc ggt cgg cat ggc gcc aac gaa    1872
Leu Leu Ser His Ala Asp Glu Arg Leu Gly Arg His Gly Ala Asn Glu
    610                 615                 620 atc aaa aac cac ccc ttc ttc cgc ggc gtg gac tgg gag acc atc cgc    1920
Ile Lys Asn His Pro Phe Phe Arg Gly Val Asp Trp Glu Thr Ile Arg
625                 630                 635                 640 cag gtc ggc gct ccc tac atc ccc aag ctg tcc agc gtc acc gac acg    1968
Gln Val Gly Ala Pro Tyr Ile Pro Lys Leu Ser Ser Val Thr Asp Thr
                645                 650                 655 cgc ttc ttc cca aca gac gag ctg gag aac gtg cca gac tct ccc gcc    2016
Arg Phe Phe Pro Thr Asp Glu Leu Glu Asn Val Pro Asp Ser Pro Ala
            660                 665                 670 atg gcg caa gcc gcc aag cag aga gaa caa atg ctc aag cag ggc ggc    2064
Met Ala Gln Ala Ala Lys Gln Arg Glu Gln Met Leu Lys Gln Gly Gly
        675                 680                 685 agc gcc gcc aac act gct cag gca aag gaa gac ctg ccc ttc atc ggc    2112
Ser Ala Ala Asn Thr Ala Gln Ala Lys Glu Asp Leu Pro Phe Ile Gly
    690                 695                 700 tac acc tac tcc agg ttc gac tac ctc acg cgg aaa aac gca ctg tag    2160
Tyr Thr Tyr Ser Arg Phe Asp Tyr Leu Thr Arg Lys Asn Ala Leu
705                 710                 715                 720

<210> SEQ ID NO 2
<211> LENGTH: 719
<212> TYPE: PRT
<213> ORGANISM: Ashbya gossypii

<400> SEQUENCE: 2

Met Phe Gly Gln Gly Tyr Tyr Gln Gly Asn Arg Asp Gln Asp Ser Pro
1               5                   10                  15

Leu Gln Arg Pro Pro Ala Ala Gln Phe Ser Ser Ala Tyr Met Glu Gln
            20                  25                  30
```

```
Gln Gly Ser His Gln Ser Leu Gln Glu His Leu Ala Tyr Glu Gln Leu
         35                  40                  45

Gln Leu Gln Gln Gln Gln Gln Gln Gln Gln His Ala Ala Pro
     50                  55                  60

His Ala Asn Gly Asp Gly Tyr Gly Ala Gly Phe Thr Asp Ile Pro Thr
 65                  70                  75                  80

Met Leu Gly Ser Val Gly Ala Pro Ser Pro Ala Phe Gln Pro Pro Met
                 85                  90                  95

Val Val Gly Met Gln Gln Gln Pro Ile Asn Thr Pro Pro Thr Ala
                100                 105                 110

Thr Ser Ile Tyr Ser Gln Asn Asn Asn Ser Phe Thr Asn Val Asn Asp
            115                 120                 125

Thr Thr Leu Ala Pro Gly His Ser Ser Pro Gly His Tyr Ser Asn Ser
130                 135                 140

Ser Asp Tyr Ser Gly Gln Gln Pro Ala Ser Ser Ala Tyr Lys Gln Phe
145                 150                 155                 160

Gly Gly Ser Glu Ser Pro Leu Gln Pro Ala Ala Leu Pro Gly Leu Leu
                165                 170                 175

Asp Gly Ser Leu Gly Asp Gln Thr Leu Val Gly Asn Gln Ser Ser Gln
                180                 185                 190

Gly Ala Met Leu Ser Arg Gln Ser Leu Gln Cys Ser Ser Val Pro Gln
                195                 200                 205

Ser Pro Asn Gly Gly Gln Arg Gln Thr Ser Gly Val Gly Asn Tyr Met
210                 215                 220

Tyr Phe Glu Arg Arg Pro Glu Leu Leu Ser Lys Ser Thr Gln Glu Lys
225                 230                 235                 240

Ala Ala Ala Val Lys Leu Lys Val Glu Asn Phe Tyr Gln Ser Ser Val
                245                 250                 255

Asn His Ala Ile Glu Arg Asn Gln Arg Arg Val Glu Leu Glu Ser Gln
                260                 265                 270

Leu Leu Ser His Gly Trp Ser Glu Glu Arg Lys Asn Arg Gln Leu Ser
            275                 280                 285

Ser Leu Gly Lys Lys Glu Ser Gln Phe Leu Arg Leu Arg Arg Thr Arg
            290                 295                 300

Leu Ser Leu Glu Asp Phe His Thr Val Lys Val Ile Gly Lys Gly Ala
305                 310                 315                 320

Phe Gly Glu Val Arg Leu Val Gln Lys Lys Asp Thr Gly Lys Ile Tyr
                325                 330                 335

Ala Met Lys Thr Leu Leu Lys Ser Glu Met Tyr Lys Lys Asp Gln Leu
            340                 345                 350

Ala His Val Lys Ala Glu Arg Asp Val Leu Ala Gly Ser Asp Ser Pro
            355                 360                 365

Trp Val Val Ser Leu Tyr Tyr Ser Phe Gln Asp Ala Gln Tyr Leu Tyr
        370                 375                 380

Leu Ile Met Glu Phe Leu Pro Gly Gly Asp Leu Met Thr Met Leu Ile
385                 390                 395                 400

Arg Trp Gln Ile Phe Thr Glu Asp Val Thr Arg Phe Tyr Met Ala Glu
                405                 410                 415

Cys Ile Leu Ala Ile Glu Ala Ile His Lys Leu Gly Phe Ile His Arg
                420                 425                 430

Asp Ile Lys Pro Asp Asn Ile Leu Ile Asp Ile Arg Gly His Ile Lys
            435                 440                 445
```

-continued

```
Leu Ser Asp Phe Gly Leu Ser Thr Gly Phe His Lys Thr His Asp Ser
    450                 455                 460

Asn Tyr Tyr Lys Lys Leu Leu Gln Glu Asp Glu Gln Gln Asn Gly
465                 470                 475                 480

Gly Asn Met Gly Lys Tyr Pro Ala Ser Gly Gly Gly Asn Gly Gly
                485                 490                 495

Gly Asn Arg Asn Thr Met Leu Val Asp Ala Ile His Leu Thr Met Thr
            500                 505                 510

Asn Arg Gln Gln Met Gln Thr Trp Arg Lys Ser Arg Arg Leu Met Ala
            515                 520                 525

Tyr Ser Thr Val Gly Thr Pro Asp Tyr Ile Ala Pro Glu Ile Phe Leu
    530                 535                 540

Tyr Gln Gly Tyr Gly Gln Glu Cys Asp Trp Trp Ser Leu Gly Ala Ile
545                 550                 555                 560

Met Tyr Glu Cys Leu Ile Gly Trp Pro Pro Phe Cys Ser Glu Thr Pro
                565                 570                 575

Gln Glu Thr Tyr Arg Lys Ile Met Asn Phe Glu Gln Thr Leu Val Phe
            580                 585                 590

Pro Asp Asp Ile His Ile Ser Tyr Glu Ala Glu Asp Leu Ile Arg Arg
            595                 600                 605

Leu Leu Ser His Ala Asp Glu Arg Leu Gly Arg His Gly Ala Asn Glu
    610                 615                 620

Ile Lys Asn His Pro Phe Phe Arg Gly Val Asp Trp Glu Thr Ile Arg
625                 630                 635                 640

Gln Val Gly Ala Pro Tyr Ile Pro Lys Leu Ser Ser Val Thr Asp Thr
                645                 650                 655

Arg Phe Phe Pro Thr Asp Glu Leu Glu Asn Val Pro Asp Ser Pro Ala
            660                 665                 670

Met Ala Gln Ala Ala Lys Gln Arg Glu Gln Met Leu Lys Gln Gly Gly
            675                 680                 685

Ser Ala Ala Asn Thr Ala Gln Ala Lys Glu Asp Leu Pro Phe Ile Gly
    690                 695                 700

Tyr Thr Tyr Ser Arg Phe Asp Tyr Leu Thr Arg Lys Asn Ala Leu
705                 710                 715

<210> SEQ ID NO 3
<211> LENGTH: 1086
<212> TYPE: DNA
<213> ORGANISM: Ashbya gossypii
<220> FEATURE:
<221> NAME/KEY: CDS
<222> LOCATION: (1)..(1086)

<400> SEQUENCE: 3 atg act tcc acg acc agt tgt gag gga tgc gaa gtc tgc aag acg ggg      48
Met Thr Ser Thr Thr Ser Cys Glu Gly Cys Glu Val Cys Lys Thr Gly
  1               5                  10                  15 gag ccg aaa tac cgc tgt ccg cgg tgc tcg cgg aga acg tgc tcg cta      96
Glu Pro Lys Tyr Arg Cys Pro Arg Cys Ser Arg Arg Thr Cys Ser Leu
             20                  25                  30 gcg tgc tct cga cag cat aag gag cag gag aac tgc tcc ggc acc agc     144
Ala Cys Ser Arg Gln His Lys Glu Gln Glu Asn Cys Ser Gly Thr Ser
         35                  40                  45 ggc cag acg acg gaa tat atc ccg cgg gga atg ctg aag ggc gcg gac     192
Gly Gln Thr Thr Glu Tyr Ile Pro Arg Gly Met Leu Lys Gly Ala Asp
     50                  55                  60
```

```
acg aag gat gaa aca aac ccg ctg gtg cag cgg gac tac aac ttc ctc        240
Thr Lys Asp Glu Thr Asn Pro Leu Val Gln Arg Asp Tyr Asn Phe Leu
 65                  70                  75                  80 ata ggc ctg aac cgg aag gtg cag ctg ctg aag gag ggc agc tcg cag        288
Ile Gly Leu Asn Arg Lys Val Gln Leu Leu Lys Glu Gly Ser Ser Gln
                 85                  90                  95 aag aat aag aac ata gtt cac gcg ggc aga ggg gat ggc ggg cac gga        336
Lys Asn Lys Asn Ile Val His Ala Gly Arg Gly Asp Gly Gly His Gly
            100                 105                 110 cgg gtg ggg aag ccc ggt agc gtg gtg cgg cgc gga gtg cgg tgc atg        384
Arg Val Gly Lys Pro Gly Ser Val Val Arg Arg Gly Val Arg Cys Met
        115                 120                 125 cta ctg ccg aag ggc atg cag agg tcg ctg tgg aac aag agc aag tgg        432
Leu Leu Pro Lys Gly Met Gln Arg Ser Leu Trp Asn Lys Ser Lys Trp
    130                 135                 140 gac aag tcg ctg gac acg ttt gtg tgg acc ata gaa tgg gca gtg gcc        480
Asp Lys Ser Leu Asp Thr Phe Val Trp Thr Ile Glu Trp Ala Val Ala
145                 150                 155                 160 cga ccc ggc ggt gag cag tgg acg cac tgc tcg cat cgg aac cag gag        528
Arg Pro Gly Gly Glu Gln Trp Thr His Cys Ser His Arg Asn Gln Glu
                165                 170                 175 caa agc agg ctg ttg gac tgt att ggc aaa gcg gtg ttc gac aag tgc        576
Gln Ser Arg Leu Leu Asp Cys Ile Gly Lys Ala Val Phe Asp Lys Cys
            180                 185                 190 gcg gag tgg ctg ccg ctg gct gcc gct ggg acg atg ggg aac ccg ctg        624
Ala Glu Trp Leu Pro Leu Ala Ala Ala Gly Thr Met Gly Asn Pro Leu
        195                 200                 205 acc aag gct agc cgg cta cag gcg ctt gtg ggg agc ggg tta cga tac        672
Thr Lys Ala Ser Arg Leu Gln Ala Leu Val Gly Ser Gly Leu Arg Tyr
    210                 215                 220 tat acg aag cag ttt cca gcc gag act gag ggt gtg ata gat aca aag        720
Tyr Thr Lys Gln Phe Pro Ala Glu Thr Glu Gly Val Ile Asp Thr Lys
225                 230                 235                 240 agg gtt gtc gag ctg gac ccg cag aag gct gtt ggg gaa ctg ttc cgg        768
Arg Val Val Glu Leu Asp Pro Gln Lys Ala Val Gly Glu Leu Phe Arg
                245                 250                 255 aac aag act gtt atc gaa ttt ccc acc gta tat atc gcg gct agt gcg        816
Asn Lys Thr Val Ile Glu Phe Pro Thr Val Tyr Ile Ala Ala Ser Ala
            260                 265                 270 gag gac atg gag cgg ctg ggc ttc agg gtt gcg tcg gat ggt act acg        864
Glu Asp Met Glu Arg Leu Gly Phe Arg Val Ala Ser Asp Gly Thr Thr
        275                 280                 285 acc tcg tcc agc gat agc agc gac acc tcg agc agc gat agc agc gat        912
Thr Ser Ser Ser Asp Ser Ser Asp Thr Ser Ser Ser Asp Ser Ser Asp
    290                 295                 300 agc tcg agc ggc gat agc tcg agc gac agc gat tca tcc tcc gat ggt        960
Ser Ser Ser Gly Asp Ser Ser Ser Asp Ser Asp Ser Ser Ser Asp Gly
305                 310                 315                 320 gag ccc gaa gag aat ccc gcg agg ttg gag cct gcg ccg ccg cct gca       1008
Glu Pro Glu Glu Asn Pro Ala Arg Leu Glu Pro Ala Pro Pro Pro Ala
                325                 330                 335 tcc ccg tca cac ggg gga gaa aca gac agc gac gat ggc tat acg cct       1056
Ser Pro Ser His Gly Gly Glu Thr Asp Ser Asp Asp Gly Tyr Thr Pro
            340                 345                 350 ggc att tcg ctc gat ttc ttg gcg gat tag                               1086
Gly Ile Ser Leu Asp Phe Leu Ala Asp
        355                 360
```

```
<210> SEQ ID NO 4
<211> LENGTH: 361
<212> TYPE: PRT
<213> ORGANISM: Ashbya gossypii

<400> SEQUENCE: 4

Met Thr Ser Thr Thr Ser Cys Glu Gly Cys Glu Val Cys Lys Thr Gly
 1               5                  10                  15

Glu Pro Lys Tyr Arg Cys Pro Arg Cys Ser Arg Thr Cys Ser Leu
                20                  25                  30

Ala Cys Ser Arg Gln His Lys Glu Gln Glu Asn Cys Ser Gly Thr Ser
            35                  40                  45

Gly Gln Thr Thr Glu Tyr Ile Pro Arg Gly Met Leu Lys Gly Ala Asp
        50                  55                  60

Thr Lys Asp Glu Thr Asn Pro Leu Val Gln Arg Asp Tyr Asn Phe Leu
 65                  70                  75                  80

Ile Gly Leu Asn Arg Lys Val Gln Leu Leu Lys Glu Gly Ser Gln
                85                  90                  95

Lys Asn Lys Asn Ile Val His Ala Gly Arg Gly Asp Gly His Gly
                100                 105                 110

Arg Val Gly Lys Pro Gly Ser Val Val Arg Arg Gly Val Arg Cys Met
            115                 120                 125

Leu Leu Pro Lys Gly Met Gln Arg Ser Leu Trp Asn Lys Ser Lys Trp
            130                 135                 140

Asp Lys Ser Leu Asp Thr Phe Val Trp Thr Ile Glu Trp Ala Val Ala
145                 150                 155                 160

Arg Pro Gly Gly Glu Gln Trp Thr His Cys Ser His Arg Asn Gln Glu
                165                 170                 175

Gln Ser Arg Leu Leu Asp Cys Ile Gly Lys Ala Val Phe Asp Lys Cys
            180                 185                 190

Ala Glu Trp Leu Pro Leu Ala Ala Gly Thr Met Gly Asn Pro Leu
                195                 200                 205

Thr Lys Ala Ser Arg Leu Gln Ala Leu Val Gly Ser Gly Leu Arg Tyr
            210                 215                 220

Tyr Thr Lys Gln Phe Pro Ala Glu Thr Glu Gly Val Ile Asp Thr Lys
225                 230                 235                 240

Arg Val Val Glu Leu Asp Pro Gln Lys Ala Val Gly Glu Leu Phe Arg
                245                 250                 255

Asn Lys Thr Val Ile Glu Phe Pro Thr Val Tyr Ile Ala Ala Ser Ala
            260                 265                 270

Glu Asp Met Glu Arg Leu Gly Phe Arg Val Ala Ser Asp Gly Thr Thr
            275                 280                 285

Thr Ser Ser Ser Asp Ser Asp Thr Ser Ser Ser Asp Ser Ser Asp
            290                 295                 300

Ser Ser Ser Gly Asp Ser Ser Asp Ser Asp Ser Ser Asp Gly
305                 310                 315                 320

Glu Pro Glu Glu Asn Pro Ala Arg Leu Glu Pro Ala Pro Pro Ala
                325                 330                 335

Ser Pro Ser His Gly Gly Glu Thr Asp Ser Asp Asp Gly Tyr Thr Pro
            340                 345                 350

Gly Ile Ser Leu Asp Phe Leu Ala Asp
            355                 360
```

-continued

```
<210> SEQ ID NO 5
<211> LENGTH: 642
<212> TYPE: DNA
<213> ORGANISM: Ashbya gossypii
<220> FEATURE:
<221> NAME/KEY: CDS
<222> LOCATION: (1)..(642)

<400> SEQUENCE: 5 atg agc aag acc gtc gga gca tct cgt ttc cgc cct gcc ggc tgg ctg         48
Met Ser Lys Thr Val Gly Ala Ser Arg Phe Arg Pro Ala Gly Trp Leu
 1               5                  10                  15 cag cgc gcg ggc tac gcc ccg cag gtg ttc gtg ttc cgc aac ctg gag         96
Gln Arg Ala Gly Tyr Ala Pro Gln Val Phe Val Phe Arg Asn Leu Glu
                20                  25                  30 tcg ggg cag gtg atc tac tcg cag ctg ccc acg ttc acg gag cgc cag        144
Ser Gly Gln Val Ile Tyr Ser Gln Leu Pro Thr Phe Thr Glu Arg Gln
            35                  40                  45 atc aac aag aac ttc tac cgc ccc aac tgg gag aac cgc aag ccg tcc        192
Ile Asn Lys Asn Phe Tyr Arg Pro Asn Trp Glu Asn Arg Lys Pro Ser
        50                  55                  60 acg cgc ccc gac atc tgg aag tgc atg gcc gtc gtc gac ctc gcc agt        240
Thr Arg Pro Asp Ile Trp Lys Cys Met Ala Val Val Asp Leu Ala Ser
 65                  70                  75                  80 cac gag gag agc gtg cgt ctg tac cag aac ctg tgc cgc ctg cgc tac        288
His Glu Glu Ser Val Arg Leu Tyr Gln Asn Leu Cys Arg Leu Arg Tyr
                 85                  90                  95 ctg cgc gag gtg ccg cag cgc aag gcc gcg gag cag ctg cgc aag cgc        336
Leu Arg Glu Val Pro Gln Arg Lys Ala Ala Glu Gln Leu Arg Lys Arg
                100                 105                 110 aac gag ttc ggc cac atc tgg tac tcc gcg cag tac cgc ccc acc tac        384
Asn Glu Phe Gly His Ile Trp Tyr Ser Ala Gln Tyr Arg Pro Thr Tyr
            115                 120                 125 acg cag gag gct gtc gcg gac ctg cgc gag tgc ctg ctg cgc gcg cgc        432
Thr Gln Glu Ala Val Ala Asp Leu Arg Glu Cys Leu Leu Arg Ala Arg
        130                 135                 140 ggc ggc gcc acc gtc cac tgg gag gac ccc tgg cgc atg ggc gac cgc        480
Gly Gly Ala Thr Val His Trp Glu Asp Pro Trp Arg Met Gly Asp Arg
145                 150                 155                 160 gcc aag cac tgg gcc gcg ctg ccc gcc gtc cag cac cag ttc ctg ccg        528
Ala Lys His Trp Ala Ala Leu Pro Ala Val Gln His Gln Phe Leu Pro
                165                 170                 175 cgc atg gcc aac gtg gct cgc gag gag agc gcc atc ctc aag cag ctc        576
Arg Met Ala Asn Val Ala Arg Glu Glu Ser Ala Ile Leu Lys Gln Leu
                180                 185                 190 ggc gag cgc gcg aag cgc gcc ttc gcc gcg ccc gcc ccg cct gcg ccc        624
Gly Glu Arg Ala Lys Arg Ala Phe Ala Ala Pro Ala Pro Pro Ala Pro
            195                 200                 205 gcg ccg caa agc ctc tga                                                 642
Ala Pro Gln Ser Leu
    210

<210> SEQ ID NO 6
<211> LENGTH: 213
<212> TYPE: PRT
<213> ORGANISM: Ashbya gossypii

<400> SEQUENCE: 6

Met Ser Lys Thr Val Gly Ala Ser Arg Phe Arg Pro Ala Gly Trp Leu
 1               5                  10                  15

Gln Arg Ala Gly Tyr Ala Pro Gln Val Phe Val Phe Arg Asn Leu Glu
                20                  25                  30
```

```
Ser Gly Gln Val Ile Tyr Ser Gln Leu Pro Thr Phe Thr Glu Arg Gln
         35                  40                  45

Ile Asn Lys Asn Phe Tyr Arg Pro Asn Trp Glu Asn Arg Lys Pro Ser
 50                  55                  60

Thr Arg Pro Asp Ile Trp Lys Cys Met Ala Val Val Asp Leu Ala Ser
 65                  70                  75                  80

His Glu Glu Ser Val Arg Leu Tyr Gln Asn Leu Cys Arg Leu Arg Tyr
                 85                  90                  95

Leu Arg Glu Val Pro Gln Arg Lys Ala Ala Glu Gln Leu Arg Lys Arg
                100                 105                 110

Asn Glu Phe Gly His Ile Trp Tyr Ser Ala Gln Tyr Arg Pro Thr Tyr
                115                 120                 125

Thr Gln Glu Ala Val Ala Asp Leu Arg Glu Cys Leu Leu Arg Ala Arg
                130                 135                 140

Gly Gly Ala Thr Val His Trp Glu Asp Pro Trp Arg Met Gly Asp Arg
145                 150                 155                 160

Ala Lys His Trp Ala Ala Leu Pro Ala Val Gln His Gln Phe Leu Pro
                165                 170                 175

Arg Met Ala Asn Val Ala Arg Glu Glu Ser Ala Ile Leu Lys Gln Leu
                180                 185                 190

Gly Glu Arg Ala Lys Arg Ala Phe Ala Ala Pro Ala Pro Pro Ala Pro
                195                 200                 205

Ala Pro Gln Ser Leu
    210

<210> SEQ ID NO 7
<211> LENGTH: 852
<212> TYPE: DNA
<213> ORGANISM: Ashbya gossypii
<220> FEATURE:
<221> NAME/KEY: CDS
<222> LOCATION: (1)..(852)

<400> SEQUENCE: 7 atg ttc gtt tct ttt tct tac cgt cct tcc atg gcg cta gct ctc ctc      48
Met Phe Val Ser Phe Ser Tyr Arg Pro Ser Met Ala Leu Ala Leu Leu
 1               5                  10                  15 gaa gcc atc ttc aac gat agc ggc tca gaa aca cag tgg atc agc aag      96
Glu Ala Ile Phe Asn Asp Ser Gly Ser Glu Thr Gln Trp Ile Ser Lys
                 20                  25                  30 tcg agc cgt cca atg gga gtt atc aat cag cca tcc ggg cag atc aag     144
Ser Ser Arg Pro Met Gly Val Ile Asn Gln Pro Ser Gly Gln Ile Lys
         35                  40                  45 ctt act aat gtg tcg ctg gtg agg ctt aag aag ggg aag aag cgg ttc     192
Leu Thr Asn Val Ser Leu Val Arg Leu Lys Lys Gly Lys Lys Arg Phe
 50                  55                  60 gaa gtt gct tgc tac cag aac aag gta cag gac tac cgt cgc ggc gtg     240
Glu Val Ala Cys Tyr Gln Asn Lys Val Gln Asp Tyr Arg Arg Gly Val
 65                  70                  75                  80 gag acc gac ctg gat gag gtg ctg cag atc aac cag gtg ttt cta aat     288
Glu Thr Asp Leu Asp Glu Val Leu Gln Ile Asn Gln Val Phe Leu Asn
                 85                  90                  95 gtg tct aag ggc cag gtt gcg tcc aac gag gac ttg aac ggg gct ttc     336
Val Ser Lys Gly Gln Val Ala Ser Asn Glu Asp Leu Asn Gly Ala Phe
                100                 105                 110 ggg aca aag gag cag gaa gtc gtc atc aag gag atc cta agc cgc gga     384
Gly Thr Lys Glu Gln Glu Val Val Ile Lys Glu Ile Leu Ser Arg Gly
                115                 120                 125
```

-continued

```
gag atc cag ttg tcc gag aag gaa cga cag cag atg cac ggg aag att    432
Glu Ile Gln Leu Ser Glu Lys Glu Arg Gln Gln Met His Gly Lys Ile
            130                 135                 140 acc aac gag ctg ctg act ctg gtt agc gcc aag tgc gtc aac cca aac    480
Thr Asn Glu Leu Leu Thr Leu Val Ser Ala Lys Cys Val Asn Pro Asn
145                 150                 155                 160 tcc aaa aag cgc tat cca cca acg atg atc cac aag gcg ctt gca gag    528
Ser Lys Lys Arg Tyr Pro Pro Thr Met Ile His Lys Ala Leu Ala Glu
                165                 170                 175 ctc aag ttt aac gtc gtg acg aat aag ccc gcg aag ctg cag gca ctt    576
Leu Lys Phe Asn Val Val Thr Asn Lys Pro Ala Lys Leu Gln Ala Leu
            180                 185                 190 gag gcc att aag ctg ctc gtg cag cgc caa atc att ccg att gct cgg    624
Glu Ala Ile Lys Leu Leu Val Gln Arg Gln Ile Ile Pro Ile Ala Arg
        195                 200                 205 gcc aag atg cga gtc aag gcg gtg ctt cca cgc gaa ggc aat gcc gag    672
Ala Lys Met Arg Val Lys Ala Val Leu Pro Arg Glu Gly Asn Ala Glu
210                 215                 220 gct att gcg caa gcc gcc tcg ctc att gcg gcg acc gag gcc gcg ccc    720
Ala Ile Ala Gln Ala Ala Ser Leu Ile Ala Ala Thr Glu Ala Ala Pro
225                 230                 235                 240 gaa agc gca acc acg tgg atg tgc aca ggc ctg atc gac cca atg aac    768
Glu Ser Ala Thr Thr Trp Met Cys Thr Gly Leu Ile Asp Pro Met Asn
                245                 250                 255 tac cgc gaa ctg gtc acg ctc tgt ggc aag tgc gga acg ctg cag gtg    816
Tyr Arg Glu Leu Val Thr Leu Cys Gly Lys Cys Gly Thr Leu Gln Val
            260                 265                 270 ctg gac atg gcg gtt ctg gac gat gcg aat cag tga                    852
Leu Asp Met Ala Val Leu Asp Asp Ala Asn Gln
        275                 280
```

<210> SEQ ID NO 8
<211> LENGTH: 283
<212> TYPE: PRT
<213> ORGANISM: Ashbya gossypii

<400> SEQUENCE: 8

```
Met Phe Val Ser Phe Ser Tyr Arg Pro Ser Met Ala Leu Ala Leu Leu
  1               5                  10                  15

Glu Ala Ile Phe Asn Asp Ser Gly Ser Glu Thr Gln Trp Ile Ser Lys
                 20                  25                  30

Ser Ser Arg Pro Met Gly Val Ile Asn Gln Pro Ser Gly Gln Ile Lys
             35                  40                  45

Leu Thr Asn Val Ser Leu Val Arg Leu Lys Lys Gly Lys Lys Arg Phe
     50                  55                  60

Glu Val Ala Cys Tyr Gln Asn Lys Val Gln Asp Tyr Arg Arg Gly Val
 65                  70                  75                  80

Glu Thr Asp Leu Asp Glu Val Leu Gln Ile Asn Gln Val Phe Leu Asn
                 85                  90                  95

Val Ser Lys Gly Gln Val Ala Ser Asn Glu Asp Leu Asn Gly Ala Phe
            100                 105                 110

Gly Thr Lys Glu Gln Glu Val Val Ile Lys Glu Ile Leu Ser Arg Gly
        115                 120                 125

Glu Ile Gln Leu Ser Glu Lys Glu Arg Gln Gln Met His Gly Lys Ile
    130                 135                 140

Thr Asn Glu Leu Leu Thr Leu Val Ser Ala Lys Cys Val Asn Pro Asn
145                 150                 155                 160
```

```
Ser Lys Lys Arg Tyr Pro Pro Thr Met Ile His Lys Ala Leu Ala Glu
            165                 170                 175

Leu Lys Phe Asn Val Val Thr Asn Lys Pro Ala Lys Leu Gln Ala Leu
        180                 185                 190

Glu Ala Ile Lys Leu Leu Val Gln Arg Gln Ile Ile Pro Ile Ala Arg
    195                 200                 205

Ala Lys Met Arg Val Lys Ala Val Leu Pro Arg Glu Gly Asn Ala Glu
210                 215                 220

Ala Ile Ala Gln Ala Ala Ser Leu Ile Ala Ala Thr Glu Ala Ala Pro
225                 230                 235                 240

Glu Ser Ala Thr Thr Trp Met Cys Thr Gly Leu Ile Asp Pro Met Asn
                245                 250                 255

Tyr Arg Glu Leu Val Thr Leu Cys Gly Lys Cys Gly Thr Leu Gln Val
            260                 265                 270

Leu Asp Met Ala Val Leu Asp Asp Ala Asn Gln
        275                 280

<210> SEQ ID NO 9
<211> LENGTH: 2382
<212> TYPE: DNA
<213> ORGANISM: Ashbya gossypii
<220> FEATURE:
<221> NAME/KEY: CDS
<222> LOCATION: (1)..(2382)

<400> SEQUENCE: 9 atg tcg ctg tcg gcc gct gcg aga gag ctg tcc gag tcg gac ttc cag      48
Met Ser Leu Ser Ala Ala Ala Arg Glu Leu Ser Glu Ser Asp Phe Gln
  1               5                  10                  15 gat att ggg ccg gcg ccc aaa ccg ccg cct gtg gcg tac aac cag acg      96
Asp Ile Gly Pro Ala Pro Lys Pro Pro Pro Val Ala Tyr Asn Gln Thr
             20                  25                  30 aag ccc ttg gtg aac tat atg agc caa atg gac ctc gga gcg aag agc     144
Lys Pro Leu Val Asn Tyr Met Ser Gln Met Asp Leu Gly Ala Lys Ser
         35                  40                  45 gga ggc aag atg cgg gct gtg cag cgc aag aag tcg ggg tgg gtg tcg     192
Gly Gly Lys Met Arg Ala Val Gln Arg Lys Lys Ser Gly Trp Val Ser
     50                  55                  60 tac aag gac gac ggg ctg ctg tcg ttt ctt tgg cag aag cgc tac atg     240
Tyr Lys Asp Asp Gly Leu Leu Ser Phe Leu Trp Gln Lys Arg Tyr Met
 65                  70                  75                  80 gtg ctg aac gac aac tac ctt tcg ctg tac aag ggc ggc tcg ggg cgc     288
Val Leu Asn Asp Asn Tyr Leu Ser Leu Tyr Lys Gly Gly Ser Gly Arg
                 85                  90                  95 gag gac gcg gtg gtg cag att ccg ctg acg tcg atc gtc agc gta tcg     336
Glu Asp Ala Val Val Gln Ile Pro Leu Thr Ser Ile Val Ser Val Ser
            100                 105                 110 cgg aac cag ttg aaa cag aac tgc ttt gag gtt gtt cgg agc agc gac     384
Arg Asn Gln Leu Lys Gln Asn Cys Phe Glu Val Val Arg Ser Ser Asp
        115                 120                 125 cgg tcg ggc gcg ccc gcg gcc ggc gcg ggc ggc gac tcg tcc aag aag     432
Arg Ser Gly Ala Pro Ala Ala Gly Ala Gly Gly Asp Ser Ser Lys Lys
    130                 135                 140 tcg gtc ttc att gcg acg aag acc gag ctg gac ctg cac acc tgg ctg     480
Ser Val Phe Ile Ala Thr Lys Thr Glu Leu Asp Leu His Thr Trp Leu
145                 150                 155                 160 gac tcg atc ttt tcc aaa tgt cct ctg ctc agt ggt gtc tca tcc ccc     528
Asp Ser Ile Phe Ser Lys Cys Pro Leu Leu Ser Gly Val Ser Ser Pro
                165                 170                 175
```

-continued

| | | |
|---|---|---|
| acc aat ttc acc cac aaa gtg cac gtg ggt ttt gat ccg gag acc ggt<br>Thr Asn Phe Thr His Lys Val His Val Gly Phe Asp Pro Glu Thr Gly<br>           180                      185                    190 | 576 |
| tcc ttt gta ggc atg ccg ttc aac tgg gag aag ctg ctg aag cat tcg<br>Ser Phe Val Gly Met Pro Phe Asn Trp Glu Lys Leu Leu Lys His Ser<br>        195                      200                    205 | 624 |
| cgg atc act ggc gag gat tgg aac aac aat tct gcc gct gtt att cag<br>Arg Ile Thr Gly Glu Asp Trp Asn Asn Asn Ser Ala Ala Val Ile Gln<br>210                      215                    220 | 672 |
| gtc ctg caa ttc tac cag gag tat aat aac ggg acc gca aca cct acg<br>Val Leu Gln Phe Tyr Gln Glu Tyr Asn Asn Gly Thr Ala Thr Pro Thr<br>225                      230                    235                    240 | 720 |
| gct cag gcc gcg gct cag gct gct ggt gca cct ggc cgt ccg ccg atg<br>Ala Gln Ala Ala Ala Gln Ala Ala Gly Ala Pro Gly Arg Pro Pro Met<br>                  245                    250                    255 | 768 |
| ttg act ctg tcg tct aac agc tcg cag gcc tct atg cag caa ata gcc<br>Leu Thr Leu Ser Ser Asn Ser Ser Gln Ala Ser Met Gln Gln Ile Ala<br>           260                      265                    270 | 816 |
| tct acg ccc cca tat tcg ggc ggc gaa atg ata ccc cag agg aag gcg<br>Ser Thr Pro Pro Tyr Ser Gly Gly Glu Met Ile Pro Gln Arg Lys Ala<br>275                      280                    285 | 864 |
| ccc acg cct cca aaa ccc gtg gtt act tcg ggg tct gcg atc cct tcc<br>Pro Thr Pro Pro Lys Pro Val Val Thr Ser Gly Ser Ala Ile Pro Ser<br>290                      295                    300 | 912 |
| gct aaa gga ggc cca aat gtc ggc gtc aca act tcg cca agt gtg cac<br>Ala Lys Gly Gly Pro Asn Val Gly Val Thr Thr Ser Pro Ser Val His<br>305                      310                    315                    320 | 960 |
| cat caa aat acg cag cat ggc aag cag caa tcg cca acg cag agt ggt<br>His Gln Asn Thr Gln His Gly Lys Gln Gln Ser Pro Thr Gln Ser Gly<br>                  325                    330                    335 | 1008 |
| cct cca aag tca cta cct cct ttg cac cgt gat gag gag gga ccg act<br>Pro Pro Lys Ser Leu Pro Pro Leu His Arg Asp Glu Glu Gly Pro Thr<br>           340                      345                    350 | 1056 |
| gct ccc ttg gga aac tcc gta tct tcg gtt gct act aag gag tcc cca<br>Ala Pro Leu Gly Asn Ser Val Ser Ser Val Ala Thr Lys Glu Ser Pro<br>                  355                    360                    365 | 1104 |
| act gaa agg ttg ttg aac aac ctt tca gaa act tcg ctt atg cag aaa<br>Thr Glu Arg Leu Leu Asn Asn Leu Ser Glu Thr Ser Leu Met Gln Lys<br>370                      375                    380 | 1152 |
| cag ctt cct gcg aag cct gtt gcg ccg cca tct tcg gtc ggc ccc gtt<br>Gln Leu Pro Ala Lys Pro Val Ala Pro Pro Ser Ser Val Gly Pro Val<br>385                      390                    395                    400 | 1200 |
| gct ccg cca ttg agg tta cag ccg caa cgc gtg gcg cca ggt agg ccc<br>Ala Pro Pro Leu Arg Leu Gln Pro Gln Arg Val Ala Pro Gly Arg Pro<br>                  405                    410                    415 | 1248 |
| gct cag cca ggt cct cac gcg cca gat acc cgt cct ggt ggt cca aac<br>Ala Gln Pro Gly Pro His Ala Pro Asp Thr Arg Pro Gly Gly Pro Asn<br>           420                      425                    430 | 1296 |
| gct atg aaa cag cag cat ggt ccg ccg gct gct gcc agc ggt caa ttg<br>Ala Met Lys Gln Gln His Gly Pro Pro Ala Ala Ala Ser Gly Gln Leu<br>435                      440                    445 | 1344 |
| ggc cca gat tcg aag aag cca gaa ggg gcc cct ggg cat ccg acg gca<br>Gly Pro Asp Ser Lys Lys Pro Glu Gly Ala Pro Gly His Pro Thr Ala<br>        450                      455                    460 | 1392 |
| gtt gcc aag aag aag aag gct gga agg cca act atg tcc aat gct gag<br>Val Ala Lys Lys Lys Lys Ala Gly Arg Pro Thr Met Ser Asn Ala Glu<br>465                      470                    475                    480 | 1440 |
| att atg act agg ctg gcg gct gtg acc ttc aac aca gat ccc agc cca<br>Ile Met Thr Arg Leu Ala Ala Val Thr Phe Asn Thr Asp Pro Ser Pro<br>                  485                    490                    495 | 1488 |

-continued

```
ttt ttt caa atg att gaa aaa gcc ggt caa ggt gca agt ggg tct gtt     1536
Phe Phe Gln Met Ile Glu Lys Ala Gly Gln Gly Ala Ser Gly Ser Val
        500                 505                 510 tat ttg gcg cag aga tta aaa ata ccc cca tat gat gag aat tct ggt     1584
Tyr Leu Ala Gln Arg Leu Lys Ile Pro Pro Tyr Asp Glu Asn Ser Gly
            515                 520                 525 gta agt cag cat gag ttg aat gat aac atc ggt gac aag gtg gcg atc     1632
Val Ser Gln His Glu Leu Asn Asp Asn Ile Gly Asp Lys Val Ala Ile
530                 535                 540 aaa cag atg att ctt tct aaa caa cca cgt aag gaa ttg ata gtt aat     1680
Lys Gln Met Ile Leu Ser Lys Gln Pro Arg Lys Glu Leu Ile Val Asn
545                 550                 555                 560 gaa att ttg gtt atg aaa gat tcg caa cat aag aat atc gtc aac ttt     1728
Glu Ile Leu Val Met Lys Asp Ser Gln His Lys Asn Ile Val Asn Phe
                565                 570                 575 ttg gaa gca tat ttg aaa aca gag gac gat ttg tgg gtt gtc atg gaa     1776
Leu Glu Ala Tyr Leu Lys Thr Glu Asp Asp Leu Trp Val Val Met Glu
            580                 585                 590 tac atg gaa ggc ggg tct ttg acg gat gtt att gaa aac tcc att ggc     1824
Tyr Met Glu Gly Gly Ser Leu Thr Asp Val Ile Glu Asn Ser Ile Gly
        595                 600                 605 agt gat gcc tct gag tct cca atg act gag cct caa att gca tac att     1872
Ser Asp Ala Ser Glu Ser Pro Met Thr Glu Pro Gln Ile Ala Tyr Ile
    610                 615                 620 gtc cgc gag acg tgt cag ggt tta aag ttt cta cat gac aaa cat atc     1920
Val Arg Glu Thr Cys Gln Gly Leu Lys Phe Leu His Asp Lys His Ile
625                 630                 635                 640 att cat agg gat atc aag tcg gat aac gtg ctt cta gat aca cat ggt     1968
Ile His Arg Asp Ile Lys Ser Asp Asn Val Leu Leu Asp Thr His Gly
                645                 650                 655 cgc gtt aaa atc acc gat ttc ggc ttt tgt gct aag tta act gat aag     2016
Arg Val Lys Ile Thr Asp Phe Gly Phe Cys Ala Lys Leu Thr Asp Lys
            660                 665                 670 aga agc aag aga gca aca atg gta ggt act cct tac tgg atg gca cct     2064
Arg Ser Lys Arg Ala Thr Met Val Gly Thr Pro Tyr Trp Met Ala Pro
        675                 680                 685 gag gtt gtc aaa cag cgg gaa tat gat gag aag gtt gat gtt tgg tcc     2112
Glu Val Val Lys Gln Arg Glu Tyr Asp Glu Lys Val Asp Val Trp Ser
    690                 695                 700 tta gga atc atg aca att gag atg cta gaa ggt gag cct ccg tac ttg     2160
Leu Gly Ile Met Thr Ile Glu Met Leu Glu Gly Glu Pro Pro Tyr Leu
705                 710                 715                 720 aat gaa gag cca tta aaa gca ttg tat tta att gcg aca aat ggt aca     2208
Asn Glu Glu Pro Leu Lys Ala Leu Tyr Leu Ile Ala Thr Asn Gly Thr
                725                 730                 735 ccc aag ttg aaa cat cca gaa ctc ttg tcc ttg gaa ata aag cgt ttc     2256
Pro Lys Leu Lys His Pro Glu Leu Leu Ser Leu Glu Ile Lys Arg Phe
            740                 745                 750 cta agt gtt tgt ctt tgc gtt gat gtc aga tac aga gct tct act gag     2304
Leu Ser Val Cys Leu Cys Val Asp Val Arg Tyr Arg Ala Ser Thr Glu
        755                 760                 765 gaa ttg tta cac cat tct ttc ttt gaa acg agc tgc gag cca gag gag     2352
Glu Leu Leu His His Ser Phe Phe Glu Thr Ser Cys Glu Pro Glu Glu
    770                 775                 780 ctg gca aac cta cta aag tgg aaa aag taa                             2382
Leu Ala Asn Leu Leu Lys Trp Lys Lys
785                 790
```

-continued

```
<210> SEQ ID NO 10
<211> LENGTH: 793
<212> TYPE: PRT
<213> ORGANISM: Ashbya gossypii

<400> SEQUENCE: 10

Met Ser Leu Ser Ala Ala Arg Glu Leu Ser Glu Ser Asp Phe Gln
 1               5                  10                  15

Asp Ile Gly Pro Ala Pro Lys Pro Pro Val Ala Tyr Asn Gln Thr
                20                  25                  30

Lys Pro Leu Val Asn Tyr Met Ser Gln Met Asp Leu Gly Ala Lys Ser
            35                  40                  45

Gly Gly Lys Met Arg Ala Val Gln Arg Lys Lys Ser Gly Trp Val Ser
        50                  55                  60

Tyr Lys Asp Asp Gly Leu Leu Ser Phe Leu Trp Gln Lys Arg Tyr Met
65                  70                  75                  80

Val Leu Asn Asp Asn Tyr Leu Ser Leu Tyr Lys Gly Gly Ser Gly Arg
                85                  90                  95

Glu Asp Ala Val Val Gln Ile Pro Leu Thr Ser Ile Val Ser Val Ser
                100                 105                 110

Arg Asn Gln Leu Lys Gln Asn Cys Phe Glu Val Val Arg Ser Ser Asp
            115                 120                 125

Arg Ser Gly Ala Pro Ala Ala Gly Ala Gly Asp Ser Ser Lys Lys
        130                 135                 140

Ser Val Phe Ile Ala Thr Lys Thr Glu Leu Asp Leu His Thr Trp Leu
145                 150                 155                 160

Asp Ser Ile Phe Ser Lys Cys Pro Leu Leu Ser Gly Val Ser Ser Pro
                165                 170                 175

Thr Asn Phe Thr His Lys Val His Val Gly Phe Asp Pro Glu Thr Gly
            180                 185                 190

Ser Phe Val Gly Met Pro Phe Asn Trp Glu Lys Leu Leu Lys His Ser
        195                 200                 205

Arg Ile Thr Gly Glu Asp Trp Asn Asn Ser Ala Ala Val Ile Gln
210                 215                 220

Val Leu Gln Phe Tyr Gln Glu Tyr Asn Asn Gly Thr Ala Thr Pro Thr
225                 230                 235                 240

Ala Gln Ala Ala Ala Gln Ala Ala Gly Ala Pro Gly Arg Pro Pro Met
                245                 250                 255

Leu Thr Leu Ser Ser Asn Ser Ser Gln Ala Ser Met Gln Gln Ile Ala
            260                 265                 270

Ser Thr Pro Pro Tyr Ser Gly Gly Glu Met Ile Pro Gln Arg Lys Ala
        275                 280                 285

Pro Thr Pro Pro Lys Pro Val Val Thr Ser Gly Ser Ala Ile Pro Ser
290                 295                 300

Ala Lys Gly Gly Pro Asn Val Gly Val Thr Thr Ser Pro Ser Val His
305                 310                 315                 320

His Gln Asn Thr Gln His Gly Lys Gln Gln Ser Pro Thr Gln Ser Gly
                325                 330                 335

Pro Pro Lys Ser Leu Pro Pro Leu His Arg Asp Glu Gly Pro Thr
            340                 345                 350

Ala Pro Leu Gly Asn Ser Val Ser Val Ala Thr Lys Glu Ser Pro
        355                 360                 365

Thr Glu Arg Leu Leu Asn Asn Leu Ser Glu Thr Ser Leu Met Gln Lys
370                 375                 380
```

```
Gln Leu Pro Ala Lys Pro Val Ala Pro Pro Ser Ser Val Gly Pro Val
385                 390                 395                 400

Ala Pro Pro Leu Arg Leu Gln Pro Gln Arg Val Ala Pro Gly Arg Pro
                405                 410                 415

Ala Gln Pro Gly Pro His Ala Pro Asp Thr Arg Pro Gly Gly Pro Asn
            420                 425                 430

Ala Met Lys Gln Gln His Gly Pro Pro Ala Ala Ser Gly Gln Leu
        435                 440                 445

Gly Pro Asp Ser Lys Lys Pro Glu Gly Ala Pro Gly His Pro Thr Ala
    450                 455                 460

Val Ala Lys Lys Lys Ala Gly Arg Pro Thr Met Ser Asn Ala Glu
465                 470                 475                 480

Ile Met Thr Arg Leu Ala Ala Val Thr Phe Asn Thr Asp Pro Ser Pro
                485                 490                 495

Phe Phe Gln Met Ile Glu Lys Ala Gly Gln Gly Ala Ser Gly Ser Val
                500                 505                 510

Tyr Leu Ala Gln Arg Leu Lys Ile Pro Pro Tyr Asp Glu Asn Ser Gly
            515                 520                 525

Val Ser Gln His Glu Leu Asn Asp Asn Ile Gly Asp Lys Val Ala Ile
    530                 535                 540

Lys Gln Met Ile Leu Ser Lys Gln Pro Arg Lys Glu Leu Ile Val Asn
545                 550                 555                 560

Glu Ile Leu Val Met Lys Asp Ser Gln His Lys Asn Ile Val Asn Phe
                565                 570                 575

Leu Glu Ala Tyr Leu Lys Thr Glu Asp Asp Leu Trp Val Val Met Glu
            580                 585                 590

Tyr Met Glu Gly Gly Ser Leu Thr Asp Val Ile Glu Asn Ser Ile Gly
        595                 600                 605

Ser Asp Ala Ser Glu Ser Pro Met Thr Glu Pro Gln Ile Ala Tyr Ile
    610                 615                 620

Val Arg Glu Thr Cys Gln Gly Leu Lys Phe Leu His Asp Lys His Ile
625                 630                 635                 640

Ile His Arg Asp Ile Lys Ser Asp Asn Val Leu Leu Asp Thr His Gly
                645                 650                 655

Arg Val Lys Ile Thr Asp Phe Gly Phe Cys Ala Lys Leu Thr Asp Lys
            660                 665                 670

Arg Ser Lys Arg Ala Thr Met Val Gly Thr Pro Tyr Trp Met Ala Pro
    675                 680                 685

Glu Val Val Lys Gln Arg Glu Tyr Asp Glu Lys Val Asp Val Trp Ser
690                 695                 700

Leu Gly Ile Met Thr Ile Glu Met Leu Glu Gly Glu Pro Pro Tyr Leu
705                 710                 715                 720

Asn Glu Glu Pro Leu Lys Ala Leu Tyr Leu Ile Ala Thr Asn Gly Thr
                725                 730                 735

Pro Lys Leu Lys His Pro Glu Leu Leu Ser Leu Glu Ile Lys Arg Phe
            740                 745                 750

Leu Ser Val Cys Leu Cys Val Asp Val Arg Tyr Arg Ala Ser Thr Glu
        755                 760                 765

Glu Leu His His Ser Phe Phe Glu Thr Ser Cys Glu Pro Glu Glu
    770                 775                 780

Leu Ala Asn Leu Leu Lys Trp Lys Lys
785                 790
```

```
<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer S1

<400> SEQUENCE: 11
gctagggata acagggtaat                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer S2

<400> SEQUENCE: 12
aggcatgcaa gcttagatct                                              20

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence:
      oligonucleotide primer G2

<400> SEQUENCE: 13
gtttagtctg accatctcat ctg                                          23

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer G3

<400> SEQUENCE: 14
tcgcagaccg ataccaggat c                                            21

<210> SEQ ID NO 15
<211> LENGTH: 65
<212> TYPE: DNA
<213> ORGANISM: Artificial Sequence
<220> FEATURE:
<223> OTHER INFORMATION: Description of Artificial Sequence:
      oligonucleotide AG007S1

<400> SEQUENCE: 15
atatgtactt cgagagacgt ccagagctac tgagcaaatc cacacgctag ggataacagg  60
gtaat                                                              65

<210> SEQ ID NO 16
<211> LENGTH: 65
<212> TYPE: DNA
<213> ORGANISM: Artificial Sequence
<220> FEATURE:
<223> OTHER INFORMATION: Description of Artificial Sequence:
      oligonucleotide AG007S2
```

-continued

```
<400> SEQUENCE: 16
gtcttcatag cgtatatttt accggtatct ttcttctgca ccagaaggca tgcaagctta    60
gatct                                                                65

<210> SEQ ID NO 17
<211> LENGTH: 70
<212> TYPE: DNA
<213> ORGANISM: Artificial Sequence
<220> FEATURE:
<223> OTHER INFORMATION: Description of Artificial Sequence:
      oligonucleotide AG008S1

<400> SEQUENCE: 17
tgtattggca aacgggtgtt cgacaagtgc gcggagtggc tgccgctggc gctagggata    60
acagggtaat                                                           70

<210> SEQ ID NO 18
<211> LENGTH: 69
<212> TYPE: DNA
<213> ORGANISM: Artificial Sequence
<220> FEATURE:
<223> OTHER INFORMATION: Description of Artificial Sequence:
      oligonucleotide AG008S2

<400> SEQUENCE: 18
gtgacgggga tgcaggcggc ggcgcaggct ccaacctcgc gggattctca ggcatgcaag    60
cttagatct                                                            69

<210> SEQ ID NO 19
<211> LENGTH: 70
<212> TYPE: DNA
<213> ORGANISM: Artificial Sequence
<220> FEATURE:
<223> OTHER INFORMATION: Description of Artificial Sequence:
      oligonucleotide AG009S1

<400> SEQUENCE: 19
gctacgcccc gcaggtgttc gtgttccgca acctggagtc ggggcaggtg gctagggata    60
acagggtaat                                                           70

<210> SEQ ID NO 20
<211> LENGTH: 70
<212> TYPE: DNA
<213> ORGANISM: Artificial Sequence
<220> FEATURE:
<223> OTHER INFORMATION: Description of Artificial Sequence:
      oligonucleotide AG009S2

<400> SEQUENCE: 20
ccatgcgcgg caggaactgg tgctggacgg cgggcagcgc ggcccagtgc aggcatgcaa    60
gcttagatct                                                           70

<210> SEQ ID NO 21
<211> LENGTH: 70
<212> TYPE: DNA
<213> ORGANISM: Artificial Sequence
<220> FEATURE:
<223> OTHER INFORMATION: Description of Artificial Sequence:
      oligonucleotide AG010S1
```

-continued

```
<400> SEQUENCE: 21
tgtcgctggt gaggcttaag aagggggaaga agcggttcga agttgcttgc gctagggata    60
acagggtaat                                                            70

<210> SEQ ID NO 22
<211> LENGTH: 69
<212> TYPE: DNA
<213> ORGANISM: Artificial Sequence
<220> FEATURE:
<223> OTHER INFORMATION: Description of Artificial Sequence:
      oligonucleotide AG010S2

<400> SEQUENCE: 22
cagagcgtga ccagttcgcg gtagttcatt gggtcgatca ggcctgtgca ggcatgcaag    60
cttagatct                                                            69

<210> SEQ ID NO 23
<211> LENGTH: 65
<212> TYPE: DNA
<213> ORGANISM: Artificial Sequence
<220> FEATURE:
<223> OTHER INFORMATION: Description of Artificial Sequence:
      oligonucleotide AG011S1

<400> SEQUENCE: 23
cggacgcaca gtaaacaggt tgctagagac ttgctagaga attaggctag ggataacagg    60
gtaat                                                                65

<210> SEQ ID NO 24
<211> LENGTH: 65
<212> TYPE: DNA
<213> ORGANISM: Artificial Sequence
<220> FEATURE:
<223> OTHER INFORMATION: Description of Artificial Sequence:
      oligonucleotide AG011S2

<400> SEQUENCE: 24
atctatcctg atctcacaaa tattaatttt atccatgaaa ttaacaggca tgcaagctta    60
gatct                                                                65
```